United States Patent
Amstislavski et al.

(10) Patent No.: US 10,604,734 B2
(45) Date of Patent: Mar. 31, 2020

(54) THERMAL INSULATION MATERIAL FROM MYCELIUM AND FORESTRY BYPRODUCTS

(71) Applicant: University of Alaska Anchorage, Anchorage, AK (US)

(72) Inventors: Philippe Amstislavski, Anchorage, AK (US); Zhaohui Yang, Anchorage, AK (US); Maria D. White, Anchorage, AK (US)

(73) Assignee: UNIVERSITY OF ALASKA ANCHORAGE, Anchorage, AK (US)

( * ) Notice: Subject to any disclaimer, the term of this patent is extended or adjusted under 35 U.S.C. 154(b) by 0 days.

(21) Appl. No.: 15/418,018

(22) Filed: Jan. 27, 2017

(65) Prior Publication Data

US 2017/0218327 A1    Aug. 3, 2017

Related U.S. Application Data

(60) Provisional application No. 62/288,156, filed on Jan. 28, 2016.

(51) Int. Cl.
| | |
|---|---|
| *C12N 1/14* | (2006.01) |
| *E04B 1/82* | (2006.01) |
| *G10K 11/162* | (2006.01) |
| *E04B 1/76* | (2006.01) |
| *E04B 1/74* | (2006.01) |
| *E01C 3/00* | (2006.01) |
| *E01C 3/06* | (2006.01) |

(52) U.S. Cl.
CPC .................. *C12N 1/14* (2013.01); *E04B 1/76* (2013.01); *E04B 1/82* (2013.01); *G10K 11/162* (2013.01); *E01C 3/003* (2013.01); *E01C 3/06* (2013.01); *E02D 2300/0071* (2013.01); *E04B 2001/745* (2013.01); *Y02A 30/245* (2018.01)

(58) Field of Classification Search
CPC ...................................................... C12N 1/14
See application file for complete search history.

(56) References Cited

U.S. PATENT DOCUMENTS

| | | | | |
|---|---|---|---|---|
| 2,034,678 | A * | 3/1936 | Knaust ............... | A01G 18/00 47/1.1 |
| 7,718,416 | B1 | 5/2010 | Zhu | |
| 8,460,897 | B1 * | 6/2013 | Bernat .................. | C12N 1/14 435/203 |
| 2008/0145577 | A1 * | 6/2008 | Bayer .................. | C05D 9/00 428/35.6 |
| 2009/0280212 | A1 | 11/2009 | Sugimoto et al. | |
| 2009/0307969 | A1 | 12/2009 | Bayer et al. | |
| 2012/0135504 | A1 | 5/2012 | Ross | |

OTHER PUBLICATIONS

Alba, P. et al., Elastic-Wave Velocities and Liquefaction Potential. Geotech Testing J. 1984; 7(2): 77-88.

Arcat, Inc. Insulfoam Specifications, Section 07210, EPS Building Insulation. www.insulfoam.com/specifications. Last accessed Jul. 5, 2017 (11 pages).

Arifin, Y. H. et al., Mycelium fibers as new resource for environmental sustainability. Procedia Engineering: Malaysian Technical Universities Conference on Engineering & Technology. 2013; 53:504-8.

ASTM D2166-13, Standard Test Method for Unconfined Compressive Strength of Cohesive Soil, ASTM International, West Conshohocken, PA. www.astm.org, 2013 (7 pages).

ASTM D5334-14, Standard Test Method for Determination of Thermal Conductivity of Soil and Soft Rock by Thermal Needle Probe Procedure, ASTM International, West Conshohocken, PA, www.astm.org, 2014 (8 pages).

Bandyopadhyay, A. et al., Studies on photocatalytic degradation of polystyrene. Mater Sci Technol. 2007; 23(3):307-14.

Cornell University, "*Ganoderma lucidum* and *G. tsugae*."(2006). p. 1, para 2. Retrieved on Jul. 5, 2017. Retrieved from <https://blog.mycology.cornell.edu/2006/10/30/introducing-ganoderma-lucidum-and-g-tsugae/> (3 pages).

Decagon Devices, Inc., Operator's Manual for KD2 Pro Thermal Properties Analyzer, Pullman WA, 2015 (71 pages).

Dyvik, R. et al., Lab Measurements of $G_{max}$ Using Bender Elements. Proc ASCE Convention on Advances in the Art of Testing Soils under Cyclic Conditions, (1985) pp. 186-196.

Eseller-Bayat, E. et al., Bender elements and bending disks for measurement of shear and compression wave velocities in large fully and partially saturated sand specimens. Geotech Testing J. 2013; 36(2):1-8.

Gareis, M., Diagnostic cell culture assay (MTT—test) for the detection of cytotoxic contaminants and residues (in German). J Consum Protect Food Safety (J. fur Verbraucherschutz and Lebensmittelsicherheit). 2006; 1:354-63 (Abstract Included).

Hanelt, M. et al., Cytotoxicity mycotoxins evaluated by the MTT-cell culture assay. Mycopathologia. 1995; 128:167-74.

Holt et al., Fungal mycelium and cotton plant materials in the manufacture of biodegradable molded packaging material: evaluation study of select blends of cotton byproducts. J Biobased Mater Bioenergy. 2012; 6:431-9.

Huang Y.C. et al., Health effects associated with faulty application of spray polyurethane foam in residential homes. Environ Res. 2014; 134:295-300.

Isikgor et al., Lignocellulosic Biomass: A Sustainable Platform for Production of Bio-Based Chemicals and Polymers. Polym. Chem. 2015; 6:4497-559; pp. 4499 and 4504.

(Continued)

*Primary Examiner* — Bin Shen

(74) *Attorney, Agent, or Firm* — Ballard Spahr LLP

(57) ABSTRACT

Disclosed are biodegradable insulation materials comprising a structural scaffold; and at least one temperature resilient fungus. Also disclosed are methods of making and using biodegradable insulation materials comprising a structural scaffold; and at least one temperature resilient fungus. For example, disclosed are methods of insulating an infrastructure comprising administering the disclosed biodegradable insulation materials to an infrastructure.

15 Claims, 13 Drawing Sheets

(56) References Cited

OTHER PUBLICATIONS

Johanning, E. et al., Toxicity screening of materials from buildings with fungal indoor air quality problems (*Stachybotrys chartarum*). Mycotoxin Res. 1998; 14: 60-73.
Kapoor et al., Studies on Different Growth Parameters of *Ganoderma lucidum*. Int J Sci Environ Technol. 2014; 3(4):1515-24.
Katsanevakis, S., Chapter 2: Marine Debris, a Growing Problem: Sources, distribution, Composition, and Impacts. Marine pollution: New Research. Ed. Tobias Hofer. Nova Science Publishers, New York, 2008 (pp. 53-62; specifically p. 59).
Lee, J.S. et al., Bender elements: performance and signal interpretation. J Geotech Geoenviron Eng. 2005; 131(9):1063-70.
Leong, E.C. et al., Measuring shear wave velocity using bender elements. Geotech Testing J. 2005; 28(5):1-11.
Padula, V.M. et al., The impacts of plastic on western Aleutian Islands seabirds: detection of phthalates in muscle and embryonic tissues, Proceedings of the 16th Alaska Bird Conference, Juneau, AK, USA; 2014 (Abstract Only—1 page).
Pan, H. et al., Formation of self-extinguishing flame retardant biobased coating on cotton fabrics via Layer-by-Layer assembly of chitin derivatives. Carbohydrate Polymers. 2015; 115: 516-524.
Pelletier, M.G. et al. An evaluation study of mycelium based acoustic absorbers grown on agricultural by-product substrates. Industrial Crops and Products. 2013; 51:480-5.
Prashanth, K.V.H. and R.N. Tharanahan, Chitin/chitosan: modifications and their unlimited application potential—an overview. Trends Food Sci Technol. 2007; 18: 117-31.
Shirley, D.J. et al., Acoustic and engineering properties of sediments. Report ARL-TR-75-58. Applied Research Laboratory, University of Texas, Austin, 1975 (68 pages).
Travaglini, S. et al., Mycology matrix composites. Proc. 28th Annu Tech Conf Amer Soc Composites. 2013; 1:517-35.
Wendler, G. et al., The Climate of Alaska for 2014. Alaska Climate Research Center, University of Alaska, Fairbanks. Alaska 2014 Statewide Climate Summary (8 pages).
Zhang, H. et al., Co-release of Hexabromocyclododecane (HBCD) and Nano- and Microparticles from Thermal Cutting of Polystyrene Foams. Environ Sci Technol. 2012; 46(20):10990-6.
International Search Report and Written Opinion dated Apr. 25, 2017 by the International Searching Authority for International Application No. PCT/US2017/015359, which was filed on Jan. 27, 2017 and published as WO 2017/132523 dated Aug. 3, 2017 (Applicant—The University of Alaska Anchorage) (11 pages).
U.S. Appl. No. 62/288,156, filed Jan. 28, 2016, Amstislavski, et al. (Univ. of Alaska).
PCT, PCT/US2017/015359 (WO 2017/132523), filed Jan. 27, 2017 (Aug. 3, 2017), Amstislavski, et al. (Univ. of Alaska).

* cited by examiner

THERMAL INSULATION MATERIAL FROM MYCELIUM AND FORESTRY BYPRODUCTS

CROSS REFERENCE TO RELATED APPLICATIONS

This application claims the benefit of U.S. Application No. 62/288,156, filed Jan. 28, 2016, which is incorporated herein by reference in its entirety.

BACKGROUND

There is a need for an efficient, cost-competitive technology to manufacture a renewable and biodegradable thermal insulation material for cold climate regions.

Polymeric foams, such as polystyrene and polyurethane, are commonly used for thermal insulation in infrastructure and housing construction in cold climates. These hydrocarbon-based materials are lightweight, hydrophobic, and resistant to photolysis. Polymeric foams do not decompose after the end of their intended use, and are problematic with respect to recycling and reuse. These polymeric foams are non-renewable and their production and use involve complex manufacturing processes, substantial energy inputs and associated waste streams. Polymeric foams have been shown to leach out or off-gas several toxins, which can bio-accumulate in fish and wildlife, presenting a well-documented environmental health problem. In most cold regions the construction materials are shipped in from the manufacturing centers, adding to an already large negative environmental effect of the polymeric insulation foams.

A renewable and biodegradable alternative to these conventional thermal insulation materials can substantially reduce environmental and health burdens of construction and promote sustainable infrastructure development. Biodegradable and renewable insulation materials are of interest to construction industry in the cold regions and globally for a range of applications. Such materials can serve as replacements for the petroleum-based polymers for a range of applications and offer several advantages over polymeric foams, including freedom from petroleum products, low energy inputs and low cost of production, fast renewability, carbon capture and storage, and bio-degradability at end of use. Though there have been a number of strategies developed to produce eco-friendly materials from mycelium by combining various fungi species with different types of biomass, their disadvantages in the fragile Arctic ecosystems range from the potential of introducing an exotic species of fungi that may negatively affect the local ecosystems, to being too slow and costly to produce, especially in the cold environments.

Due to the high cost of the transportation of the polymeric foam and due to the lack of recycling and landfill services for its disposal in the many areas of the Circumpolar North, local production of a cost-competitive, renewable, and biodegradable insulation material could be the most sustainable approach to meeting the needs of the infrastructure and population needs.

BRIEF SUMMARY

Disclosed are biodegradable insulation materials comprising a structural scaffold comprising a nutritive media for fungal mycelium and at least one temperature resilient fungus.

Disclosed are biodegradable insulation materials comprising a structural scaffold comprising a nutritive media for fungal mycelium and at least one temperature resilient fungus, wherein the structural scaffold can be three-dimensional.

Disclosed are biodegradable insulation materials comprising a structural scaffold comprising a nutritive media for fungal mycelium and at least one temperature resilient fungus, wherein the structural scaffold comprises a biomass. In some instances, the biomass can be pasteurized. In some instances, the structural scaffold further comprises a biomass feedstock.

Disclosed are biodegradable insulation materials comprising a structural scaffold comprising a nutritive media for fungal mycelium and at least one temperature resilient fungus, wherein the structural scaffold comprises a structural reinforcement.

Disclosed are biodegradable insulation materials comprising a structural scaffold comprising a nutritive media for fungal mycelium and at least one temperature resilient fungus, wherein the biodegradable insulation material comprises the net shape of the object to be insulated. In some instances, the biodegradable insulation material comprises the net shape of a cylinder, tube, circle, oval, rectangle, or square. In some instances, the structural scaffold comprises the net shape of the object to be insulated.

Disclosed are biodegradable insulation materials comprising a structural scaffold comprising a nutritive media for fungal mycelium and at least one temperature resilient fungus, wherein the structural scaffold comprises a biopolymer or synthetic polymer that is non-toxic to the fungus and withstands moisture and humidity. In some instances the biopolymer can be a cellulose-based biopolymer filament.

Disclosed are biodegradable insulation materials comprising a structural scaffold comprising a nutritive media for fungal mycelium and at least one temperature resilient fungus, wherein the scaffold is colonized by mycelium of the temperature resilient fungus.

Disclosed are biodegradable insulation materials comprising a structural scaffold comprising a nutritive media for fungal mycelium and at least one temperature resilient fungus, further comprising mycelium from a second temperature resilient fungus.

Disclosed are biodegradable insulation materials comprising a structural scaffold comprising a nutritive media for fungal mycelium and at least one temperature resilient fungus, wherein the at least one temperature resilient fungus is a fungus that remains biologically viable within a temperature range of +40° to −50° C. In some instances, the temperature resilient fungus can be a saprotrophic Basidiomycete. In some instances, the saprotrophic Basidiomycete can belong to one of the polypore genera, such as *Irpex*. An example of an *Irpex* species is *Irpex lacteus*.

Also disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional.

Disclosed are methods for producing a biodegradable insulation material comprising forming a structural scaffold; inoculating the structural scaffold with a culture of at least one temperature resilient fungus in the presence of a nutritive media under environmental conditions that allow for mycelium growth; and allowing mycelium of the temperature resilient fungus to colonize the scaffold, wherein the environmental conditions that allow for mycelium growth comprise exposure of the mycelium to carbon dioxide gas in the range of 400-1,000 ppm. In some instances, the environmental conditions that allow for mycelium growth comprise exposure of the mycelium to temperatures of 0° to 21° C. In some instances, the environmental conditions that allow for mycelium growth comprise exposure of the mycelium to variable relative humidity. In some instances, the environmental conditions that allow for mycelium growth comprise exposure of the mycelium to variable lighting. In some instances, the environmental conditions that allow for mycelium growth comprise exposure of the culture, the mycelium and the scaffold to variable pressure.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein allowing the mycelium of the temperature resilient fungus to colonize the scaffold comprises incubating the scaffolds for a period of 4 to 14 days.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising pressing the scaffold colonized by mycelium of the temperature resilient fungus to achieve desired density, thermal conductivity, elastic moduli, Young's modulus, compressive strength, and thickness.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising machining the scaffold colonized by mycelium of the temperature resilient fungus to achieve desired net form and thickness.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising allowing the biodegradable insulation material to form a chitinous hydrophobic outer skin.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising drying the scaffold colonized with mycelium of the temperature resilient fungus. In some instances, the drying comprises temperatures of at least 60° C.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the temperature resilient fungus is a fungus that remains biologically viable after the exposure to temperatures of less than 0° C.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the temperature resilient fungus is a saprotrophic Basidiomycete. In some instances, the saprotrophic Basidiomycete can belong to one of the polypore genera, such as *Irpex*. An example of an *Irpex* species is *Irpex lacteus*.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material has a self-skinning property.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material comprises two or more of the temperature resilient fungus mycelium colonized scaffolds.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprises adding to the biodegradable insulation material a non-cytotoxic deterrent to vermin and competing fungi and mold species.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising layering the biodegradable insulation material to produce flexible or rigid laminated panels.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material has a thermal conductivity, elastic, shear and Young's moduli, and compressive strength comparable to synthetic polymeric foams.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material is free of cytotoxic metabolites or compounds.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is formed by: blending a feedstock comprising biomass to form a blend; pasteurizing the blend; cooling the blend; forming the blend into the desired shape; and incubating the blend under conditions favorable for mycelium growth.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional, wherein the three-dimensional scaffold can be formed using a 3D printer. In some instances, the three-dimensional scaffold comprises biopolymer or synthetic polymers. For example, the biopolymer or synthetic polymers can be cellulose-based filaments.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional, wherein the scaffold is formed by a 3D printing process within a mold or enclosure that allows for a desired shape. In some instances, the mold or desired shape can be determined based on the object or area to be insulated with the biodegradable insulation material.

Also disclosed are methods of insulating an infrastructure comprising introducing the disclosed biodegradable insulation materials to the infrastructure.

Disclosed are methods of insulating an infrastructure comprising introducing the disclosed biodegradable insulation materials to an infrastructure, wherein the infrastructure is underlayment for oil and gas pipeline foundations, large civil infrastructure, road underpayment, housing, piping systems, above ground and underground environmental controls and sensors, and backfill in road construction.

Disclosed are methods of insulating an infrastructure comprising introducing the disclosed biodegradable insulation materials to an infrastructure, wherein the temperature resilient fungus is already found in the environment in which the infrastructure is present.

Disclosed are methods of insulating an infrastructure comprising introducing the disclosed biodegradable insulation materials to an infrastructure, wherein the introduction occurs by placing the biodegradable insulation material around the object to be insulated or spraying the biodegradable insulation material on the object to be insulated.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
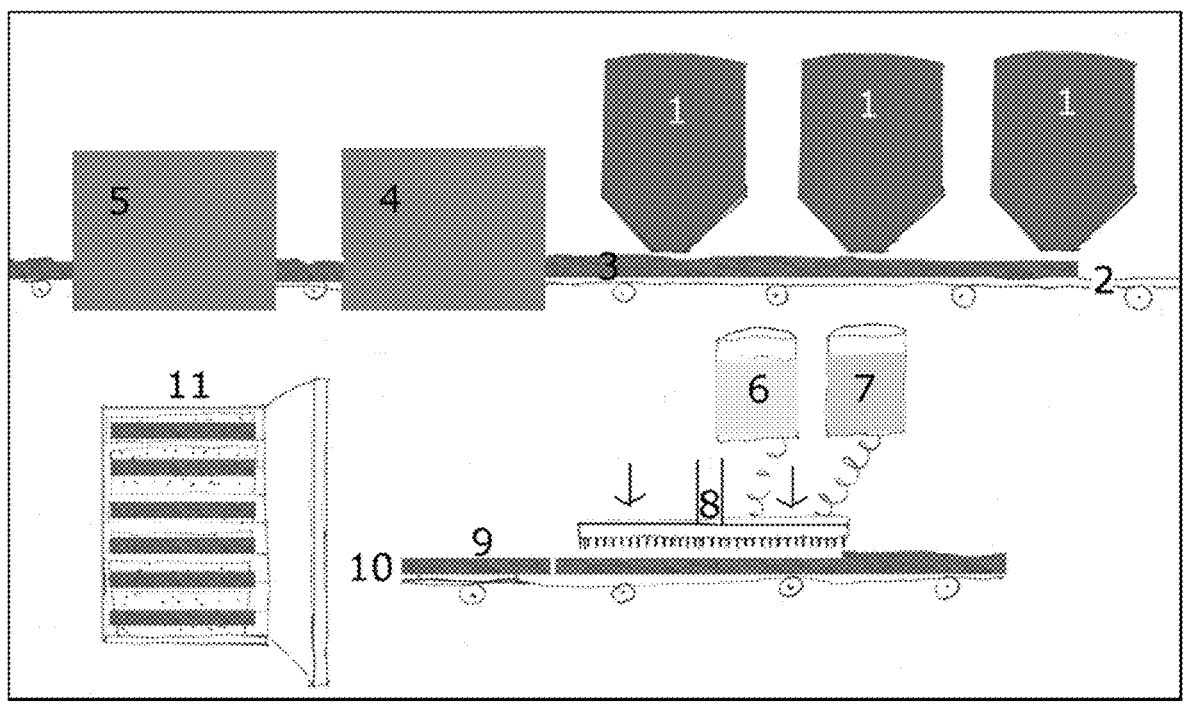
FIG. 1 shows a schematic drawing of the bioengineering process for a biodegradable insulation material: 1 feedstock hampers, 2—conveyer belt, 3—blended feedstock moving on the conveyer belt, 4—pasterization chamber, 5—cooling chamber, 6—culture fermenter, 7—cleaning solution tank, 8—printer head with inoculant broth (method 2), 9—inoculated and pressed-down material, 10—terminus of the conveyer belt, 11—incubation chamber.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular fungi species or their strains, and reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a scaffold is disclosed and discussed and a number of modifications that can be made to a number of materials including the scaffolds are discussed, each and every combination and permutation and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, fungi species or strains, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a scaffold" includes a plurality of such scaffolds, reference to "the scaffold" is a reference to one or more scaffolds and equivalents thereof known to those skilled in the art, and so forth.

The phrase "temperature resilient fungus" refers to a fungus that remains biologically viable in temperatures +40° to −50° C. Temperature resilient fungi can continue to grow in sub-freezing temperatures. For example, mycelium from these fungi remain biologically viable and can grow at temperatures of less than 0° C.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Biodegradable Insulation Material

Disclosed are biodegradable insulation materials comprising a structural scaffold and at least one temperature resilient fungus.

Disclosed are biodegradable insulation materials comprising a structural scaffold and at least one temperature resilient fungus, further comprising a non-cytotoxic deterrent to vermin and competing fungi species. Non-cytotoxic deterrents can be, but are not limited to monoterpenes, essential oils, and *Eutrema japonicum*. The non-cytotoxic deterrent can be incorporated within the biodegradable insulation material or can be coated on the outside of the biodegradable insulation material. In some instances, vermin can include, but are not limited to, rodents, insects, and competing fungi species.

Disclosed herein are compositions and methods, that involve growing a fungal species endemic to the cold regions on a nutrient and cellulose-rich scaffold, and in some instances subjecting it to a pressure and thermal treatment. The resultant chitin-based biodegradable insulation material is renewable, bio-degradable, and has been shown to be safe for humans and the environment. Standard cytotoxicity bioassay testing on the samples of resultant material has shown that the material has no cytotoxic compounds or metabolites.

Its physical, environmental health and safety, and mechanical properties make biodegradable insulation materials an excellent candidate for eco-friendly thermal insulation and for other light-weight fill materials in geoengineering. Specifically, bench testing showed that the protocol can be used to rapidly produce a thermally insulating biodegradable insulation material that can perform in some of the most challenging environments on the planet, with temperatures ranging from −50 to +30 degrees C.

Utilizing novel 3D printing methods and microbiology techniques, described herein are methods of developing a structurally sound, "self-healing" material with thermal conductivity properties comparable to the conventional polymeric foams. Several innovative elements of the disclosed biodegradable insulation materials set them apart from other developments in the field and allow for a greater degree of thermal insulation and superior strength, while simultaneously drastically reducing the density of the material: 1) introduction of an internal structural scaffold that is also a source of nutrients for the growing mycelium; 2) direct application of the biologically-active slurry for insulation in locations where direct contact with the soil is expected; 3) protocol to produce a self-healing, hydrophobic skin to prevent water-logging; 4) incubation process to produce specified thermal and mechanical properties; and 5) producing thin layers of the material and allowing them to fuse together by placing them in close proximity to produce a campsite material with desired properties.

Currently used composite materials that utilize mycelia of various of fungi grown through wood sawdust and other agricultural and forestry byproducts are rapidly renewable and biodegradable. The combination of these characteristics with the carbon footprint and the low amount of energy needed in the manufacturing process makes fungal mycelium composites attractive to the packaging industry.

The mechanical properties of a mycelium-based composite using *Ganoderma lucidum* fungus grown through an enriched sawdust substrate was investigated. The study found that their mycelium-based composite was performing similarly to the polymeric foams. It exhibited the compressive strength almost 3 times the tensile strength, which attests to the potential of their methods to produce various mycelium-based composites for biodegradable packaging. However, this study as well as several others also reported that the exposure to moisture rapidly decreases the performance of these mycelium-based composites.

The effect of different feedstock blends on the physical properties of resulting mycelium-based composites was studied. An optimization of the biomass feedstock the particle size to improve colonization of the substrate by the mycelium was reported to be effective for production of material used for packaging applications. Their findings included data on the evaluation on the physical properties of the resultant material. Based on these findings a process was developed which uses agricultural biomass and fungi culture to produce an eco-friendly packaging and insulating board. Cost analysis showed that that such materials could be cost-competitive with the conventional packaging, when considering production, shipping and operation, installation, and remediation costs associated with the polymeric alternatives.

However, these composites have distinct disadvantages that make them unusable for infrastructure thermo-insulation across different temperatures for several reasons. Fungal species reported to be used for manufacture of mycelium-based materials originate from the warm regions and thus their mycelium grows well at temperatures close to +22 degrees Centigrade. This is far above the mean annual temperature in many cold climate regions including Alaska, where the spatial mean annual air temperature in 2014 was −4.4 degrees Centigrade, consistent with other areas in the Circumpolar North. When exposed to colder temperatures, these species and strains of fungi found in the warmer climates typically become dormant or become biologically inert and their rate of substrate colonization either slows to a glacial pace or stops. While it is technically possible to maintain in-mold temperatures close to 22 degrees Centigrade during the manufacturing process, with the average temperatures at −4.4 degrees Centigrade, the steep thermal gradient between the ambient and the in-mold temperature needed for incubation will require very large energy inputs, most likely from the hydrocarbon sources. This would deny the mycelium-based materials its key environmental advantage over the polymeric foams—that of being carbon-neutral or negative. Therefore a new process is required to produce composites produced using one of these species for in situ applications for off-site manufacturing in the colder temperatures.

There is a risk of introducing exotic and potentially invasive species of fungi into the local ecosystem associated with these fungi composites. Use of a species of fungi already found in the region directly addresses this concern.

Thermal conductivity values of the existing mycelium-based material are between 0.18 and 0.10 W/(m·K). These conductivity values were within the ranges of gypsum (0.17), high-density hardboard (0.15), plywood (0.12), hardwoods (0.16), and softwoods (0.12). They are inferior to the extruded polymeric foams such as polystyrene and polyurethane, and are inadequate for most cold climates applications, where lower thermal conductivity is needed.

1. Scaffolds

Disclosed herein are biodegradable insulation material comprising a structural scaffold. Structural scaffolds can include, or can have added to it, a nutritive media for fungal mycelium. Disclosed herein are biodegradable insulation materials comprising a structural scaffold wherein the structural scaffold comprises a nutritive media for fungal mycelium and at least one temperature resilient fungus. In some instances where the structural scaffold comprises a nutritive media for fungal mycelium, the structural scaffold can be considered the source of nutrients for a temperature resilient fungus. Nutritive medias for fungal mycelium are well known in the art, for example, they can be, but are not limited to, potato dextrose agar or sabouraud agar. In some instances, a second nutrient or nutritive media can be added to the structural scaffold.

Disclosed are biodegradable insulation materials comprising a structural scaffold, wherein the structural scaffold is three-dimensional. Also disclosed are biodegradable insulation materials comprising a structural scaffold comprising a nutritive media for fungal mycelium; and at least one temperature resilient fungus, wherein the structural scaffold is three-dimensional.

Disclosed are biodegradable insulation materials comprising a structural scaffold comprising a nutritive media for fungal mycelium; and at least one temperature resilient fungus, wherein the structural scaffold comprises a biomass. In some instances, the biomass is pasteurized. In some instances, the structural scaffold comprises a biomass feedstock. The biomass or biomass feedstock can comprise a nutritive media for fungal mycelium. In some instances, the structural scaffold can be coated with a nutritive media for fungal mycelium.

Disclosed are biodegradable insulation materials comprising a structural scaffold comprising a nutritive media for fungal mycelium; and at least one temperature resilient fungus wherein the structural scaffold comprises a structural reinforcement. In some instances, the structural reinforcement can consist of ceramic, polymeric, metal, or cellulose filaments that are interwoven to form a three-dimensional structure or/and a mesh.

Disclosed are biodegradable insulation materials comprising a structural scaffold comprising a nutritive media for fungal mycelium; and at least one temperature resilient fungus, wherein the biodegradable insulation material comprises the net shape of the object to be insulated. In some instances, it is the structural scaffold that comprises the net shape of the object to be insulated. The object to be insulated can be, but is not limited to, a flat surface, a round surface, or a rectangular surface. Thus, in some instances, the biodegradable insulation material or the structural scaffold can comprise the net shape of a sphere, cylinder, cube, cuboid, cone, slab, pyramid, and of non-rigid 3D shapes. In other words, the biodegradable insulation material or the structural scaffold can be molded, pressed, grown, or formed in any manner to any shape or size.

Disclosed are biodegradable insulation materials comprising a structural scaffold comprising a nutritive media for fungal mycelium; and at least one temperature resilient fungus, wherein the structural scaffold comprises a biopolymer or synthetic polymer that is non-toxic to the fungus and withstands moisture and humidity and a nutritive media layer. For example, a biopolymer can be, but is not limited to, a cellulose-based biopolymer filament, polynucleotide, polypeptide, or polysaccharide. A synthetic polymer can be, but is not limited to, nylons, polythenes, polyethylenes, polyvinyl chlorides, polystyrenes, polyamides, polyesters, polyurethanes, polysulfides, polycarbonates, or silicone.

2. Fungus

Disclosed are biodegradable insulation materials comprising a structural scaffold comprising a nutritive media for fungal mycelium; and at least one temperature resilient fungus, wherein the scaffold is colonized by mycelium of the temperature resilient fungus. In some instances, the mycelium can be present on or throughout the scaffold.

In some instances, the disclosed biodegradable insulation materials further comprise mycelium from a second temperature resilient fungus. The second temperature resilient fungus can be any temperature resilient fungus that is different of the temperature resilient fungus originally present in the biodegradable insulation material. For example, it can be a temperature resilient fungus of a different genus or different species.

Disclosed are biodegradable insulation materials comprising a structural scaffold comprising a nutritive media for fungal mycelium; and at least one temperature resilient fungus, wherein the at least one temperature resilient fungus is a fungus that remains biologically viable within a temperature range of +30° to −50° C.

Disclosed are biodegradable insulation materials comprising a structural scaffold comprising a nutritive media for fungal mycelium; and at least one temperature resilient fungus, wherein the temperature resilient fungus is a saprotrophic Basidiomycete. In some instances, the saprotrophic Basidiomycete can be a polypore. For example, the polypore can be, but is not limited to, *Irpex lacteus*. In some instances, a temperature resistant Polypore already present in environments such as Alaska and the Circumpolar North can be the *Irpex lacteus* strain US Forest Service, Center for Forest Mycology Research FP-102064-Sp, strain FP-102220-Sp.

C. Methods of Making

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold. In some instances, inoculating the structural scaffold with at least one temperature resilient fungus in the presence of a nutritive media under environmental conditions that allow for mycelium growth can include a structural scaffold comprising the nutritive media or the addition of nutritive media to the structural scaffold at the time of inoculating the structural scaffold with the at least one temperature resilient fungus.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the inoculum comprises mycelium from at least two temperature resilient fungi. The second temperature resilient fungus can be added at the same time or at a different time as a first temperature resilient fungus. For example, the second temperature resilient fungus can be added hours or days after the first temperature resilient fungus is added or provided. When at least two temperature resilient fungi are present the at least two temperature resilient fungi can be different species from the same genus or from a different genus.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional.

In some instances, environmental conditions that allow for mycelium growth comprise exposure of the mycelium to carbon dioxide gas in the range of 400-2,000 ppm. Carbon dioxide conditions that are too high can prevent mycelium growth and ultimately kill the temperature resilient fungus. In some instances, environmental conditions that allow for mycelium growth comprise exposure of the mycelium to temperatures of +4° to 21° C. In some instances, mycelia can remain biologically viable at lower temperatures but they will not continue to grow. In some instances, environmental conditions that allow for mycelium growth comprise exposure of the mycelium to variable relative humidity. For example, the relative humidity can be 50%, 55%, 60%, 65%, 70%, 75%, 80%, 85%, 90%, 95%, or 100%.

In some instances, allowing the mycelium of the temperature resilient fungus to colonize the scaffold comprises incubating the scaffolds from 1 day to 30 days. In some instances, allowing the mycelium of the temperature resilient fungus to colonize the scaffold comprises incubating the scaffolds for a period of 4 to 14 days. In some instances, the period of time for incubating the scaffolds can depend on the desired thermal conductivity and mechanical properties needed for the specific location application of the biodegradable insulation material.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising pressing the scaffold colonized by mycelium of the temperature resilient fungus to achieve desired density, thermal conductivity, elastic moduli, Young's modulus, compressive strength, and thickness. The thickness can depend on location and temperature. For example, the thickness can vary based on how much room is present in the infrastructure to be insulated. In some instances, the thickness can be 2.5 cm to 10 cm. The density can be in a range of 20-250 kg/m$^3$ depending on the applications.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising machining the scaffold colonized by mycelium by cutting, pressing, and sanding of the temperature resilient fungus to achieve desired net form and thickness.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising allowing the biodegradable insulation material to form a chitinous hydrophobic outer skin. Controlling environmental conditions including, but not limited to, lighting temperature, and relative humidity can allow for formation of a chitinous hydrophobic outer skin. In some instances, allowing the biodegradable insulation material to form a chitinous hydrophobic outer skin comprises machining or cutting the scaffold or placing the incubating scaffold next to a glass or synthetic polymer surface so that the mycelium self-skins when it comes into physical contact with the said surface during the incubation under similar environmental conditions to those that allow for mycelium growth. Two or more structural scaffolds can be joined to form a single larger structural scaffold by placing the two or more structural scaffolds in close proximity so that the chitinous hydrophobic outer skin can grow from one structural scaffold to another.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising drying the scaffold colonized with mycelium of the temperature resilient fungus. Drying the scaffold can result in rendering the fungus or mycelium biologically inert, or at least preventing further growth of the mycelium. In some instances, drying comprises temperatures above 50° C. For example, drying can comprise temperatures of at least 60° C. In some instances, the amount of time needed for drying can vary based on the net thickness or density of the biodegradable insulation material. In some instances, drying the scaffold does not occur and instead the method of making the biodegradable insulation materials comprises maintaining a low environmental humidity so that the mycelium remains biologically viable and capable of vegetative growth and self-healing if damaged during or after installing or applying the biodegradable insulation material to the location or object of interest.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the temperature resilient fungus is a fungus that remains biologically viable within a temperature range of +30° to −50° C. In some instances, the temperature resilient fungus is a fungus that remains biologically viable at temperatures of less than 0° C. Therefore, temperature resilient fungi can remain viable under freezing conditions.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the temperature resilient fungus is a saprotrophic Basidiomycete. In some instances, the saprotrophic Basidiomycete can be a polypore. For example, the polypore can be, but is not limited to, *Irpex lacteus*. In some instances, a temperature resistant Polypore already present in environments such as Alaska and the Circumpolar North can be the *Irpex lacteus* strain, US Forest Service, Center for Forest Mycology Research FP-102064-Sp, or strain FP-102220-Sp.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material has a self-skinning property. While the inside of the colonized scaffold resembles an open-cell foam, the hyphae on its exposed outer surfaces form a solid face with hydrophobic properties, comprising a self-skinning process.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material comprises two or more of the temperature resilient fungus mycelium colonized scaffolds. Two or more structural scaffolds can be joined to form a single larger structural scaffold by placing the two or more structural scaffolds in close proximity so that the chitinous hydrophobic outer skin can grow from one structural scaffold to another.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprises adding to the biodegradable insulation material a non-cytotoxic deterrent to vermin and competing fungi species. Non-cytotoxic deterrents can be, but are not limited to, monoterpenes, essential oils, and *Eutrema japonicum*. Adding a non-cytotoxic deterrent includes, but is not limited to, incorporating the deterrent within the biodegradable insulation material or structural scaffold or coating the deterrent on the outside of the biodegradable insulation material. In some instances, vermin can include, but are not limited to, rodents, insects, and competing fungi species.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, further comprising layering the biodegradable insulation material to produce flexible or rigid laminated panels. Layering the biodegradable insulation material can comprise two or more of the disclosed biodegradable insulation materials layered one on top of the other or beside each other. In some instances, the two or more biodegradable insulation material can be identical or different. In some instances, each of the two or more biodegradable insulation materials can be different in terms of each comprising mycelium from a different temperature resilient fungus, each comprising a different structural scaffold, or a combination therefore. In some instances, layering comprises a scaffold core with fiber-reinforced panel outer surfaces.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material has a thermal conductivity, density, elastic, shear and Young's moduli, and compressive strength comparable to synthetic polymeric foams.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the biodegradable insulation material is free of cytotoxic metabolites or compounds. The presence of cytotoxic metabolites or compounds can be determined by an effect based colorimetric bioassay or by other methods which enable the detection of such compounds.

1. Stamping

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is formed by blending a feedstock comprising biomass to form a blend; pasteurizing the blend; cooling the blend; forming the blend into the desired shape; incubating the blend under conditions favorable for mycelium growth.

In some instances, cooling the blend occurs rapidly. For example, the cooling occurs in seconds, minutes, or hours. In some instances, cooling can occur in 1, 2, 3, 4, 5, 10, 15, 20, 25, 30, 35, 40, 45, 50, 55, or 60 minutes. In some instances cooling can occur in 1, 2, 3, 4, 5, 6, 7, 8, 9, 10, 15, 20 or 24 hours.

In some instances, forming the blend into the desired shape comprises stamping/pressing or putting into a mold. The desired shape can be determined based on the location or object to be insulated.

In some instances, conditions favorable for mycelium growth comprise exposure of the mycelium to carbon dioxide gas in the range of 400-2,000 ppm. Carbon dioxide conditions that are too high can prevent mycelium growth and ultimately kill the temperature resilient fungus. In some instances, environmental conditions that allow for mycelium growth comprise exposure of the mycelium to temperatures of +4° to 21° C. In some instances, mycelia can remain biologically viable at lower temperatures but they will not continue to grow. In some instances, environmental conditions that allow for mycelium growth comprise exposure of the mycelium to variable relative humidity. For example, the relative humidity can be 50%, 55%, 60%, 65%, 70%, 75%, 80%, 85%, 90%, 95%, or 100%.

2. 3D Printing

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional, wherein the three-dimensional scaffold is formed using a 3D printer. In some instances, the three-dimensional scaffold can comprise biopolymers or synthetic polymers. For example, a biopolymer can be, but is not limited to, a cellulose-based biopolymer filament, polynucleotide, polypeptide, or polysaccharide. A synthetic polymer can be, but is not limited to, nylons, polythenes, polyethylenes, polyvinyl chlorides, polystyrenes, polyamides, polyesters, polyurethanes, polysulfides, polycarbonates, or silicone.

Disclosed are methods for producing a biodegradable insulation material comprising forming a structural scaffold; inoculating the structural scaffold with at least one temperature resilient fungus in the presence of a nutritive media under environmental conditions that allow for mycelium growth; and allowing mycelium of the temperature resilient fungus to colonize the scaffold, wherein the structural scaffold is three-dimensional, wherein the scaffold is formed by a 3D printing process within a mold or enclosure that allows for a desired shape. In some instances, the mold or desired shape can be determined based on the object or area to be insulated with the biodegradable insulation material. The object to be insulated can be, but is not limited to, a flat surface, a round surface, or a rectangular surface. Thus, in some instances, the biodegradable insulation material or the structural scaffold can comprise the net shape of a sphere, cylinder, cube, cuboid, cone, slab, pyramid, and of non-rigid 3D shapes. In other words, the biodegradable insulation material or the structural scaffold can be printed, molded, pressed, grown, or formed in any manner to any shape or size.

D. Methods of Using

Disclosed are methods of insulating an infrastructure comprising introducing the biodegradable insulation material of any one of the disclosed biodegradable insulation materials to an infrastructure. For example, disclosed are methods of insulating an infrastructure comprising introducing to an infrastructure a biodegradable insulation materials comprising a structural scaffold comprising a nutritive media for fungal mycelium; and at least one temperature resilient fungus. In some instances, an infrastructure can be, but is not limited to, underlayment for oil and gas pipeline foundations, large civil infrastructure, road underpayment, wall insulation in buildings, piping systems, above ground and underground environmental controls and sensors, and backfill in road construction. The biodegradable insulation material can also be used in manufacture of mobile coolers and freezer units, disposable fish and food shipping containers, acoustic insulation boards, floating buoys in nets and other commercial fishing gear, buoys, textiles, and enclosures for floating sensors and logging units for environmental monitoring and automated reporting for applications in the remote and marine environments. In some instances, the infrastructures being insulated with the disclosed biodegradable insulation material are infrastructures that are present or are used in temperatures below freezing.

Disclosed are methods of insulating an infrastructure comprising introducing to an infrastructure a biodegradable insulation materials comprising a structural scaffold comprising a nutritive media for fungal mycelium; and at least one temperature resilient fungus, wherein the temperature resilient fungus is endemic to or already occurs in the environment in which the infrastructure is present. The use of endemic fungus prevents a potentially negative effect on an ecosystem by a species that was not previously present. An introduced species of fungus could alter the ecosystem and have negative impacts. Thus, it is beneficial to use a fungal strain native or endemic to the environment being treated or insulated. In some instances, a temperature resistant Polypore already present in environments can be the *Irpex lacteus* USFS strain FP-102064-Sp, or strain FP-102220-Sp.

Disclosed are methods of insulating an infrastructure comprising introducing to an infrastructure a biodegradable insulation materials comprising a structural scaffold comprising a nutritive media for fungal mycelium; and at least one temperature resilient fungus, wherein the administering occurs by placing the biodegradable insulation material around the object to be insulated or spraying the biodegradable insulation material on the object to be insulated. Units of the biodegradable insulation material can be placed under or around the object that is being insulated. Units of the biodegradable insulation material can be interlocking to form a closely fitted mold around the object. Two or more units of the biodegradable insulation material can form a "clamshell" interlocking around the object that is being insulated. Additionally, units of the biodegradable insulation material that remains biologically viable can be placed under or around the object that is being insulated so that the outer skin of the units is absorbed within the cellular structure of the biodegradable insulation material forming a larger self-healing unit.

E. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the disclosed biodegradable insulation materials, the kit comprising a structural scaffold and a nutritive media for fungal mycelium. The kits also can contain a temperature resilient fungus.

EXAMPLES

F. Example 1

1. Biodegradable Insulation Material

Under proper environmental conditions, the use of the disclosed biodegradable insulation material as thermal insulation between the thermally conductive infrastructure element (e.g., embankment under an elevated pipeline, roadway, or a building foundation) and the cold or frozen ground is more beneficial than inclusion of the polymeric foams used today for several reasons. It is rapidly renewable and biodegradable, which makes it uniquely desirable in hard-to-reach, remote areas, and ecologically sensitive habitats of the Arctic, the Antarctic, and in the marine environments, with no landfill services available. In some instances, the biodegradable insulation material includes 3D scaffolds, self-healing properties, and hydrophobic skin that prevents water-logging, and an incubation process to produce the said thermal and mechanical properties. A schematic sketch of a proposed bioengineering process is provided in FIG. 1. Unlike materials derived from trees, which require several years of growth, the proposed material can be produced in 1 to 2 weeks from inoculation of the blend with fungal culture to the final product.

The overall goal of this Example is to develop a biodegradable insulation material that uses fungal mycelium to provide thermal insulation to infrastructure in cold regions. There are three innovative processes in this invention: Process 1: the development of the manufacturing process from inoculation and incubation to final product processing. This process includes an advanced system for controlled process to optimize energy use. Process 2: Adaptation of an existing 3D printing technology to produce scaffolds that can be interfaced with the growing mycelium for maximum strength and insulation, and Process 3: Innovation in material properties of the resultant biodegradable insulation material.

i. Process 1: Development of the Manufacturing Process

This manufacturing process of a biodegradable insulation material involves several stages: biomass feedstock production; pasteurization of the feedstock; inoculation of the feedstock with culture of suitable white-rot fungi (for example, *Irpex* sp.); shaping of the inoculated feedstock slurry into desired 3D shapes through application of pressure and 3D-printing technology; incubation of the resultant product; and post-processing of the final product.

A process was developed of producing virtually any shape form of the biodegradable insulation material because the nutrient slurry can be shaped into any 3D shape, as long as the geometry permits the propagation of the vegetative mycelium through the nutritive matrix (FIG. 1). The method involves a standardized process to produce a material with known thermal insulation, mechanical and biophysical properties by employing a saprotrophic fungus, typically a Basidiomycete. The process begins with blending of the feedstock consisting of biomass, such as macerated wood with calcium sulfate, cereal grain bran, and water. The hampers containing the ingredients required for producing this blend discharge them onto a conveyer belt. The blend is then pasteurized and rapidly cooled to reduce the number of potentially competing organisms. The blend continues to move on the conveyer belt and is subjected to shaping into the final net shape and to inoculation with the liquid culture.

Two distinctive methods can be used to shape and inoculate the material (please refer to Scaffold methods 1 and 2) to produce internal scaffolds. The pressed bend is then cut into blocks and placed into an incubation chambers for a period of 7 to 14 days. In the incubation chambers, humidity, $CO_2$ concentration, and temperature are closely controlled to facilitate most favorable conditions for vegetative mycelium propagation through the pressed blend. After the incubation process is completed, the blocks become hydrophobic due to the self-skinning properties of the fungus. Self-skinning occurs when a solid face, film-like barrier produced by the mycelium when it encounters a non-nutritive barrier. This self-skinning property produces a self-healing, hydrophobic skin that prevents water-logging.

The fungus can be kept biologically active, and the blocks of the resultant open-cell foam are transported to the construction site and applied without additional treatments, thus minimizing the energy demand. A process of joining single units of the biodegradable insulation material into more complex shapes by placing them in physical contact and allowing the hyphae to bridge the gap between the units was developed. The skin is absorbed into the mycelium's overall cellular structure, creating a single larger unit.

For other applications where biomass expansion is not desirable, the fungal mycelium is rendered biologically inert by heating the blocks to 60 degrees centigrade or higher in a dryer during the manufacturing process.

ii. Process 2: Innovative 3D Internal Scaffolds

One of the aspects of the compositions and methods described herein is introduction of a structural scaffold that also provides a source of nutrients for the growing mycelium. There are several benefits of this new approach. Firstly, it affords greater degree of thermal insulation, superior strength, while simultaneously drastically reducing the density of the material.

Secondly, higher precision in controlling the thermal, mechanical, and fire retardant properties of the resultant biodegradable insulation material during the manufacturing process is critical because it affords the manufacturer to program the shape and material properties needed for a specific application (i.e., thermally insulated concrete pavement, pipe insulation, foundation insulation) by specifying the scaffold's thickness, porosity, nutrient content, shape and other variables that effect the biodegradable insulation material's performance for a given application.

The technique currently used in production of mycelium-based materials relies on packing of various biomass blends and of the inoculant into disposable plastic molds for incubation of the mix to allow the fungus to convert part of the biomass into mycelium and to shape into the final product. However, this method produces a material that is fairly dense and fragile. This method also does not permit to control the matrix to achieve the desired degree of thermal conductivity. In addition, once this material is made biologically inert it can be easily water-logged once cut.

Because 3D printing technology can produce internal scaffolds of virtually any shape and thickness, it liberates the manufacturing process from molds and permits manufacturing of virtually any shape. Depending on the application, two related scaffold methods for biodegradable insulation material production can be used.

Figure 2:
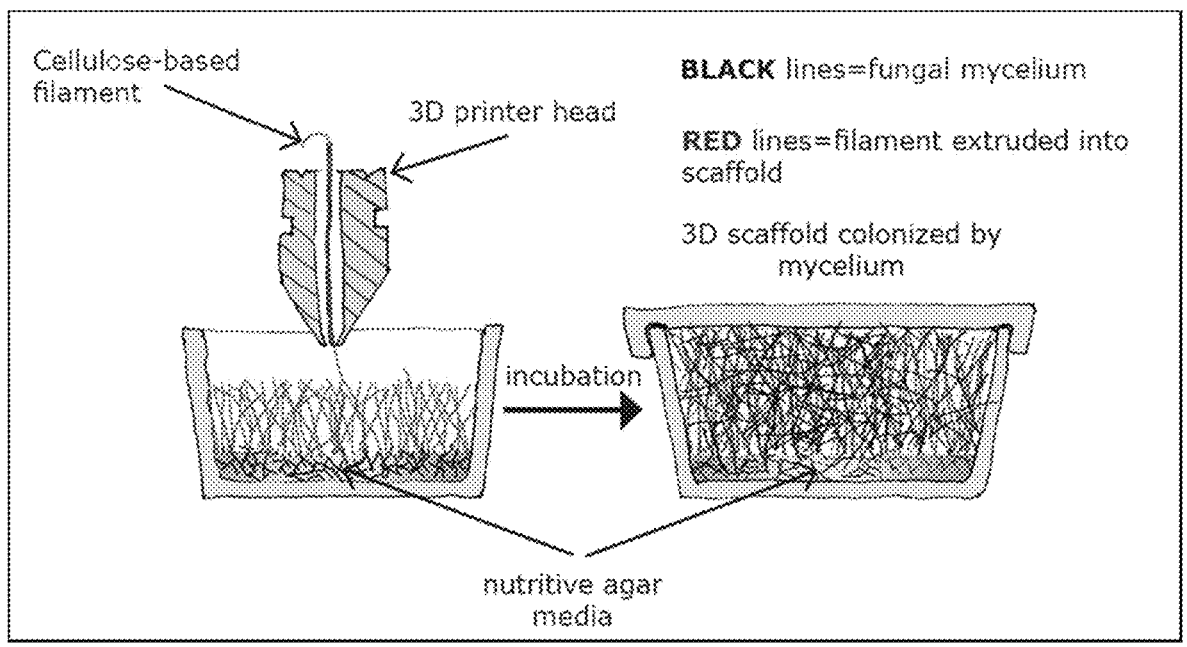
FIG. 2 shows a sectional view of the experimental design of a scaffold created by 3D printing. A light, cellulose-based scaffold is expected to reduce the weight and thermal conductivity of the biodegradable insulation material without detrimental impact on its mechanical properties.

Scaffold Method 1: The filament that is used to print the scaffold would combine structural and nutritive properties (FIG. 2). The addition of the internal scaffold will result in a lighter material of superior strength and of low thermal conductivity. As the rapidly growing fungus quickly colonizes the scaffold, it becomes an embedded and structural part of the biodegradable insulation material.

Figures 3A, 3B, 3C:
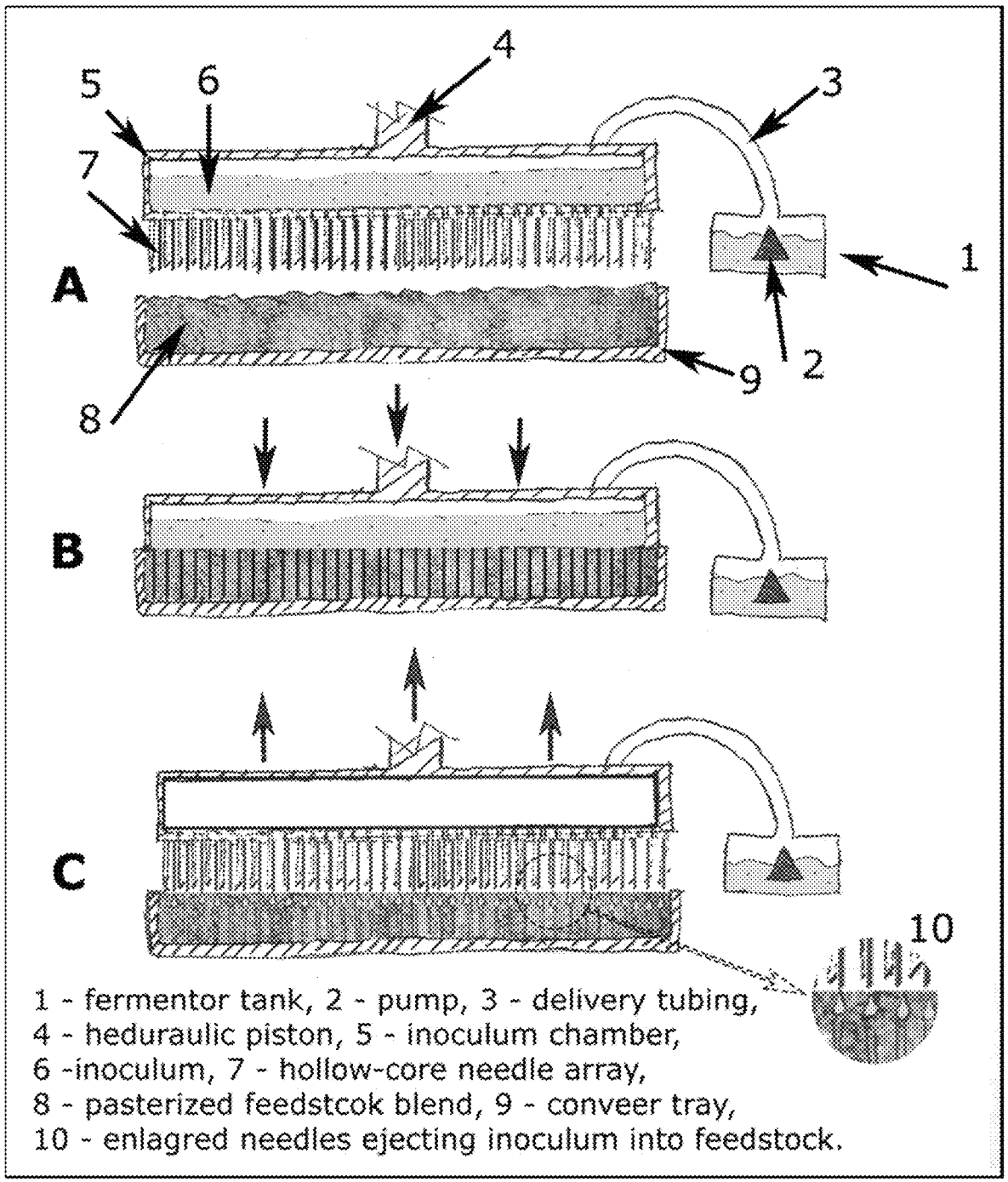
FIGS. 3A, 3B, and 3C show the process of shaping and inoculating cuboid shaped scaffolds to produce insulation boards. A—initial position of chamber; B—chamber is lowering to press feedstock into final shape and to create inoculation channels; C—chamber is lifting from the feedstock surface and ejecting inoculum into the channels.

Scaffold Method 2: The second method of producing the scaffolds is by employing a mechanism that stamps the blend into the desired net shape as it moves on the conveyer belt (Item 8 in FIG. 1 and FIG. 3). An aerobic liquid culture fermenter tank is fitted with a pump, which delivers inoculum aseptically into the stamping chamber, equipped with an array of hollow-core needles. The hydraulic piston pushes the chamber toward the blended feedstock on the belt. As the chamber is lowered, the needles create channels for the inoculum. As the chamber is lifted, the hollow-core needle array begins to gradually eject the liquid culture into the blend. This process is repeated to create a pattern of equally spaced injections that facilitate rapid colonization of the feedstock by the fugal mycelium.

The 3D scaffolds can be printed in a variety of sizes and geometries. They can be designed to bend and move with the deformation of the ground or/and the structure. Thanks to the higher tensile strength, the embedment of the scaffold into mycelium can improve other mechanical properties of the resulting material. While others have proposed insulating materials from fungi and from other organisms, this approach differs in its incorporation of 3D scaffolds, removal of the raw feedstock of inconsistent quality, and the tailoring the material for use in cold environments. Once produced, 3D printed scaffolds can be mass-stamped in the production and open exciting possibilities for producing biodegradable insulation materials in any desired size and shape. With predictable material properties, 3D-printed scaffolds make the implementation and control easy and repeatable.

Furthermore, the proposed approach features a robust, yet flexible manufacturing system designed for the ease of quality control and monitoring of the production of uniform material. The implementation requires no complicated components and can be installed in a hangar.

iii. Process 3: Innovation in Material Properties of the Resultant Foam

Microcombustion calorimetry tests showed that cotton fabrics coated with chitin, the structural component of a biodegradable insulation material, had a significantly lower peak heat-release rate and total heat-release values compared with that of uncoated cotton fabric. Thus, the biodegradable insulation material can have similar fire-retardant properties.

Six blending protocols were investigated and characterized the production, thermal and mechanical properties of the resulting biofoam. Results show that thermal conductivity of biofoam samples (n=60) averaged 0.0533 ±0.004 W/(m·K), density 220 ±38.98 kg/m³, shear modulus 7.4±4.95 (MPa), Young's modulus 21.18 ±16.21 (MPa), and compressive strength 150.83 ±113.8 (kPa). One blending protocol produced the highest shear and Young's moduli, and compressive strength, while its thermal conductivity is comparable to other groups.

Samples of biodegradable insulation material produced with *Irpex* sp. Fungus, grown on birch sawdust feedstock, were sent to an independent laboratory for toxicology analysis.

Methods: The MTT-cell culture assay with swine kidney target cells is an effect based colorimetric bioassay which enables the detection of cytotoxic metabolites produced by toxigenic fungi and other cytotoxic compounds. Extracts with organic solvents were prepared of 3 samples (with duplicates) and log2-dilutions tested in the MTT-cell culture assay.

Based on the results of bioassay analysis there was no evidence for the presence of cytotoxic compounds in the biodegradable insulation material samples. The target cells responses towards duplicates of crude extracts and control without fungus were identical. The $IC_{50}$-values were 62.5 and 125.0 mg/ml, indicating that no cytotoxic metabolites originated from culturing the fungus on this particular medium. In summary, the data obtained provides no indication for occurrence of cytotoxic compounds/metabolites in the samples tested.

Comparison of properties of biodegradable insulation materials with these of expanded polystyrene, a material widely used for building and infrastructure insulation in cold climates, is appropriate. Compressive strength of bioengineered biodegradable insulation materials is comparable to that of expanded polystyrene, thermal is slightly higher, and the density is higher. The findings indicate that mycelia-based biodegradable insulation material is a viable alternative to polymeric thermal insulation materials under extreme Northern environmental conditions.

G. Example 2

1. Introduction

Polymeric foams, such as polystyrene and polyurethane, are commonly used for thermal insulation in infrastructure and housing construction, particularly in cold climates. These hydrocarbon-based materials are lightweight, hydrophobic, and resistant to photolysis. They are not subject to decomposition or decay, and create problems with respect to recycling, reuse, and landfill operation. More importantly, these polymeric foams are non-renewable and their production and use involve complex manufacturing processes, substantial energy inputs and associated waste streams. Polymeric foams have been shown to leach out or off-gas several toxins that bio-accumulate in fish and wildlife, presenting a well-documented environmental and public health problem. A renewable alternative to today's conventional thermal insulation materials would substantially reduce environmental and public health burden of construction and promote sustainable infrastructure development.

Mycelium, the vegetative part of fungus, is a hollow structure consisting of a mass of branching, hollow tubular, chitinous hyphae which provide a fast growing, safe and inert material as the matrix for a new generation of natural foams, or biofoams. As the mycelium grow, a network of branching hyphae, primarily composed of chitin, binds together the nutritive substrate consisting of biomass and creates a vast three-dimensional matrix. The biodegradable insulation materials can serve as replacements for the petroleum based-polymeric materials for applications in insulation, packaging, noise control, and sandwich panels. Biodegradable insulation materials offer several advantages over polymeric foams, including freedom from petroleum products, low cost production, fast renewability, carbon capture and storage and bio-degradability at its end of life use. Several studies in this front have revealed the unique mechanical properties and the promising potentials of biofoam biodegradable insulation materials in engineering applications. The impact of mixing ratio of rice husks and wheat grain on the physical properties, microstructure and porosity of a mycelium biodegradable insulation material was investigated. The manufacturing of biodegradable molded packaging materials based on fungal mycelium and cotton plant materials was investigated and they found that these materials met or exceeded like characteristics of extruded polystyrene foam. The acoustic performance of a mycelium biodegradable insulation material based on agricultural by-product substrates was evaluated and results suggested an optimal performance in automotive road noise control. The elastic and strength properties of mycelium biodegradable insulation material in both tension and compression were investigated and found the strength of the biodegradable insulation material decreases with increasing moisture content, and the compressive strength is almost three times the tensile strength. The flexural properties of mycology matrix core sandwich composites by four-point bend testing were also investigated.

Presented herein are bioengineering processes for the development of a fungal mycelium-based biodegradable insulation material and characterization of its physical, thermal and mechanical properties. Test results including dry density, thermal conductivity, Young's and shear moduli, stress-strain relationship, failure mode, and compressive strength are presented. The effectiveness of the processes, and impact of packing condition and addition of natural fiber are discussed here.

2. Description of Bioengineering Process

Several mixing, packing and incubating protocols have been explored. Table 1 specifies the groups according to the mixing, packing and incubating protocols. Three batches of samples, designated as SP, SL and SPL respectively, were tested to evaluate the effectiveness of the incubation protocol and test status on the properties. The samples are right cylinders with a diameter of about 5 cm and a height of about 6 cm formed by polycarbonate tubular molds. Samples in SP and SL were incubated for two weeks, while samples in SPL were the same as SL except that they were incubated for additional four weeks before testing. All samples except those in SL were dried in an oven set at 60° C. for 24 hours before testing. It is worthy of noting that only difference between SP and SL is that samples in SP are dried, while samples in SL are live, and the difference between SP and SPL is the additional four week incubation applied to samples in SPL. Each batch had 30 samples, which were divided into six groups (G1-G6) to evaluate various blends of the biomass materials as a substrate and packing conditions for colonization of selected white-rot saprotrophic fungi cultures harvested from Alaska in molds. The blends comprised macerated sawdust pulp of Alaska birch (*Betula neoalaskana*) of 5 mm or smaller in size, millet grain, wheat bran, a natural fiber and calcium sulfate.

TABLE 1

Group specification according to mixing, packing and incubating protocols

| Group No. | Sample No. | Mixing Protocol | Packing | Incubation Time/Wks | Test Status |
|---|---|---|---|---|---|
| SP1 | G1: SP01~SP05 | I | Dense | Two | Dried |
| SP2 | G2: SP06~SP10 | I | Loose | Two | Dried |
| SP3 | G3: SP11~SP15 | II | Dense | Two | Dried |
| SP4 | G4: SP16~SP20 | II | Loose | Two | Dried |
| SP5 | G5: SP21~SP25 | III | Dense | Two | Dried |
| SP6 | G6: SP26~SP30 | III | Loose | Two | Dried |
| SL1 | G1: SL01~SL05 | I | Dense | Two | Live |
| SL2 | G2: SL06~SL10 | I | Loose | Two | Live |
| SL3 | G3: SL11~SL15 | II | Dense | Two | Live |
| SL4 | G4: SL16~SL20 | II | Loose | Two | Live |
| SL5 | G5: SL21~SL25 | III | Dense | Two | Live |
| SL6 | G6: SL26~SL30 | III | Loose | Two | Live |
| SPL1 | G1: SPL01~SPL05 | I | Dense | Six | Dried |
| SPL2 | G2: SPL06~SPL10 | I | Loose | Six | Dried |
| SPL3 | G3: SPL11~SPL15 | II | Dense | Six | Dried |
| SPL4 | G4: SPL16~SPL20 | II | Loose | Six | Dried |
| SPL5 | G5: SPL21~SPL25 | III | Dense | Six | Dried |
| SPL6 | G6: SPL26~SPL30 | III | Loose | Six | Dried |

Figure 4:
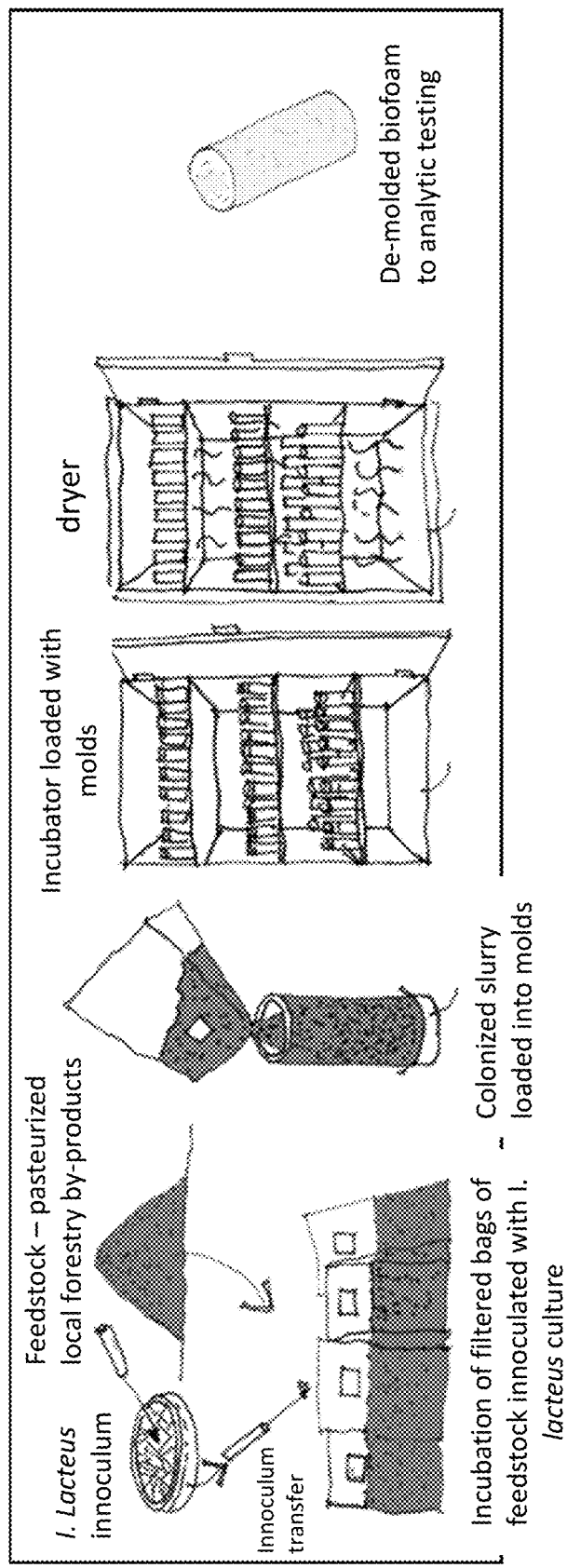
FIG. 4 shows a schematic of bioengineering process for Mixing Protocol II samples.

In Mixing Protocol I, the feedstock ingredients (substrate) and live fungi culture are mixed and packed in molds, and then placed in temperature and moisture controlled incubator. In Mixing Protocol II, the substrate and the fungi culture was incubated in filtered polypropylene bags for a defined period before the blend is macerated and packed into the cylindrical molds, permitting it re-knit into a more structurally uniform and denser foam. Mixing Protocol III is the same as Protocol I but with natural fiber (50% of substrate's dry weight) added during mixing. Two packing conditions have been applied: loose and dense, the former being naturally deposited without compaction and the latter with approximately twice the original volume of materials packed. FIG. 4 illustrates the complete bioengineering process for Group 3 samples. Birch sawdust from the local forestry industry and added nutrients were mixed with certain amount of water and pasteurized. Then the slurry was inoculated with a culture of a Basidiomycete saprotrophic fungus, present in Alaska and incubated for a certain period of time to achieve full colonization of the nutritive substrate by vegetative mycelium. The inoculated slurry was either mixed and loaded into cylindrical molds for further incubation (Protocols 1 and 3) or in Protocol II, the inoculated substrate was incubated in filtered polypropylene bags for a defined period, after which it was macerated and re-packed into the cylindrical molds. The incubation took place within a defined humidity and temperature range. The samples were dried in a dryer before de-molding for testing.

3. Testing Procedures

Tests were conducted to obtain the dry density, thermal conductivity, Young's and shear moduli, and unconfined compressive strength. The Transient Line Heat Source method built in KD2 Pro Thermal Analyzer (Decagon Devices, Inc. 2015) was used to measure thermal conductivity. The KD2 Pro complies fully with ASTM D5334-14 (ASTM, 2014). The KS-1 needle with a diameter of 1.3 mm and a length of 6 cm has a valid range of thermal conductivity from 0.02 to 2.00 W/(m·K) and was used in this study. During the tests, the needle was inserted into the sample from the top or bottom surface.

The compressive strength was obtained by unconfined compression tests according to ASTM Standard D2166-13 (ASTM, 2013). Displacement control with a vertical strain rate of 2%/min was applied. Note one exception from the ASTM standard: the sample diameter to height ratio was larger than 1:2 due to equipment limitation. However, sufficient lubricant was applied to the sample ends to minimize the end effect on strength. The Young's and shear moduli were measured by shear wave (S-wave) or compressional wave (P-wave) velocity method as described below.

i. Experiment Set-Up for Elastic Modulus Measurement

The application of S-wave or P-wave velocity methods for measuring the elastic moduli of civil engineering materials have become increasingly popular for the convenience and the non-intrusiveness of the testing method. In these methods, piezoelectric bender elements (BE) or piezoelectric disk elements (PDE) are employed to generate and detect the first arrival of S-wave or P-wave traveling through the subject material, therefore enabling the measurement of S-wave or P-wave velocity if the travel distance is known. Based on the elastic wave propagation theory, the modulus at small-strain can be calculated by the following equations:

$$G = \rho V_S^2 \quad (1)$$

$$E = \rho V_P^2 \quad (2)$$

where G is the shear modulus, E is the Young's modulus, $\rho$ is the mass density, $V_S$ is the S-wave velocity, and $V_P$ is the P-wave velocity.

Figure 5:
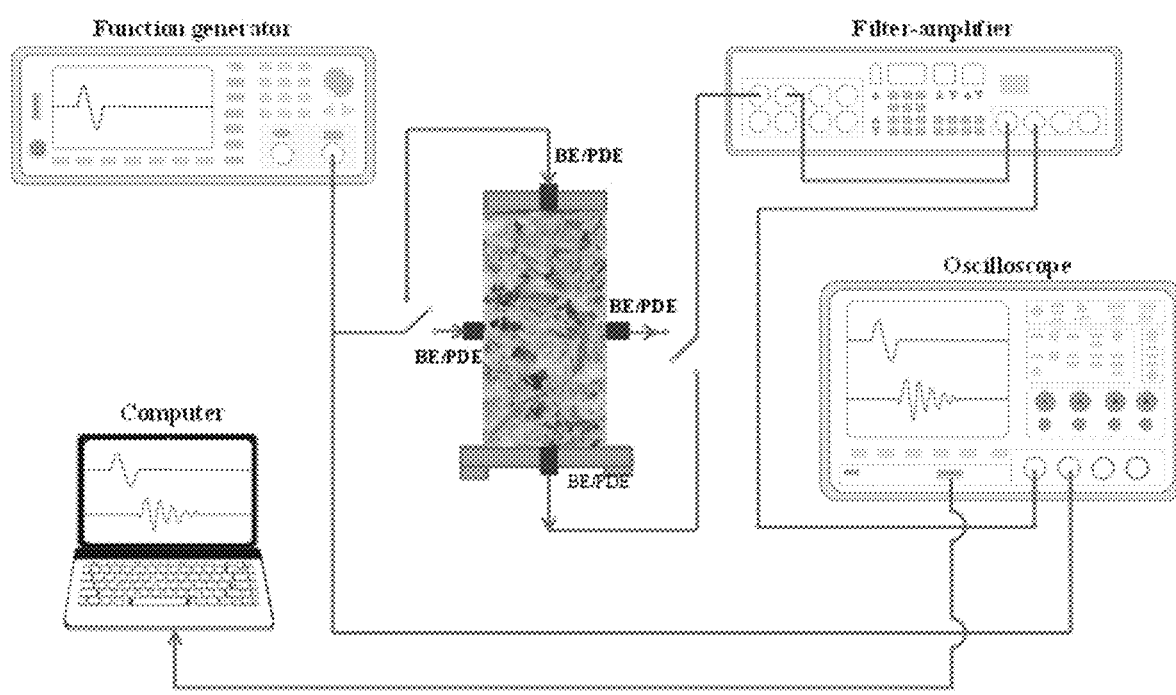
FIG. 5 shows a diagram of wave velocity test set-up.

FIG. 5 illustrates the experiment set-up for elastic moduli measurement. This set-up consists of a Function Generator (Agilent model 33521A), a power amplifier with filter (Krohn-Hite model 3364), and a Mixed Signal Oscilloscope (Agilent model 70104B). The Function Generator was used to apply a sine or a step excitation signal with a peak-to-peak amplitude of 1 V for S-wave velocity test and 4 V for P-wave velocity test. The received signal was filtered by a bandpass filter with the bandwidth frequency in 500 Hz to 50 kHz and amplified accordingly. Finally, the Oscilloscope is used to acquire the wave signal data, which was compared with the excitation signal for travel time measurement.

As illustrated in FIG. 5, two pairs of BEs were laid in top-to-bottom direction and in diameter direction at the middle sample height to measure S-wave velocity in vertical (VVS) and horizontal direction (VHS), respectively. Similarly two pair of PDEs were used to measure the P-wave velocity in vertical (VVP) and horizontal direction (VHP), respectively.

ii. Wave Velocity Determination

Figure 6:
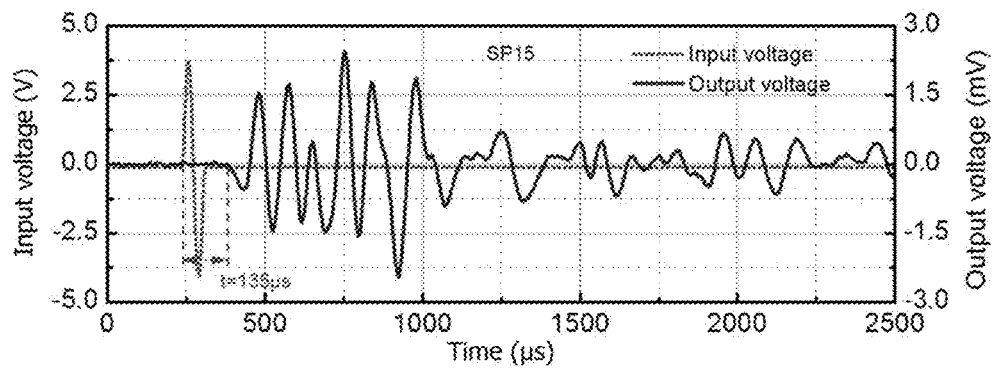
FIG. 6 shows the determination of P-wave first arrival for Sample SP15 in vertical direction.
Figure 7:
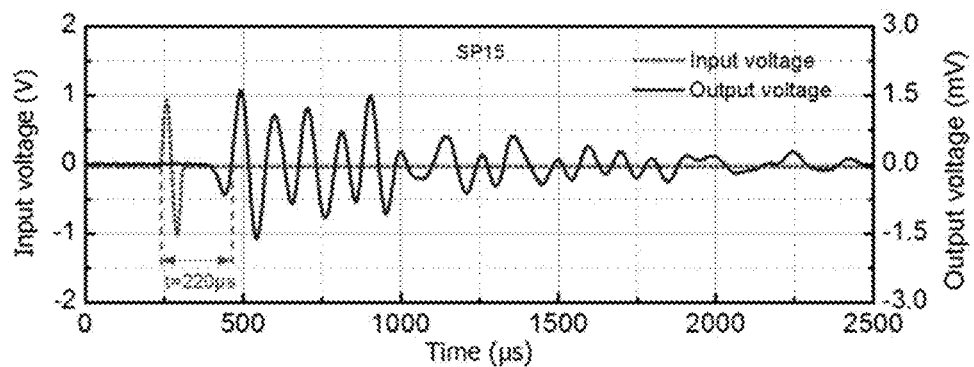
FIG. 7 shows the determination of S-wave first arrival for Sample SP15 in vertical direction.

Travel length and travel time need to be determined for evaluating wave velocity. The travel length is determined by measuring the tip-to-tip distance between the transmitter and receiver sensors. The time domain analysis method is used to determine the travel time. The P-wave first arrival is determined by the initial arrival of transmitted P-wave as it is much faster than any S-waves in the system, as shown in FIG. 6. The determination of S-wave first arrival is more difficult due to near-field effects, interference from faster P-waves in the system and other factors. There are a number of ways to minimize the error involved in S-wave first arrival determination and the zero after first bump method was used, as illustrated in FIG. 7. However, the total travel time determined as illustrated is the net travel time in the sample as there are system delays in the peripheral electronics, which can be measured by contacting the tips of the transmitter and the receiver sensors. The system delay to should be subtracted from the total travel time. The wave velocity is calculated using the following equation:

$$V = L/\Delta t = L/(t - t_o) \quad (3)$$

where V is the wave velocity, L is the travel distance, $\Delta t$ is the net travel time, t is the total travel time, $t_o$ is the system delay.

4. Results and Analyses

This section presents and analyzes the results from various tests conducted for the three batches of samples. It is noted that only elastic moduli and thermal properties were measured for SL samples as this batch was later incubated for an additional four weeks (as identified as SPL) for further testing.

i. Sample Description and Failure Modes

Figures 8A, 8B, 8C:
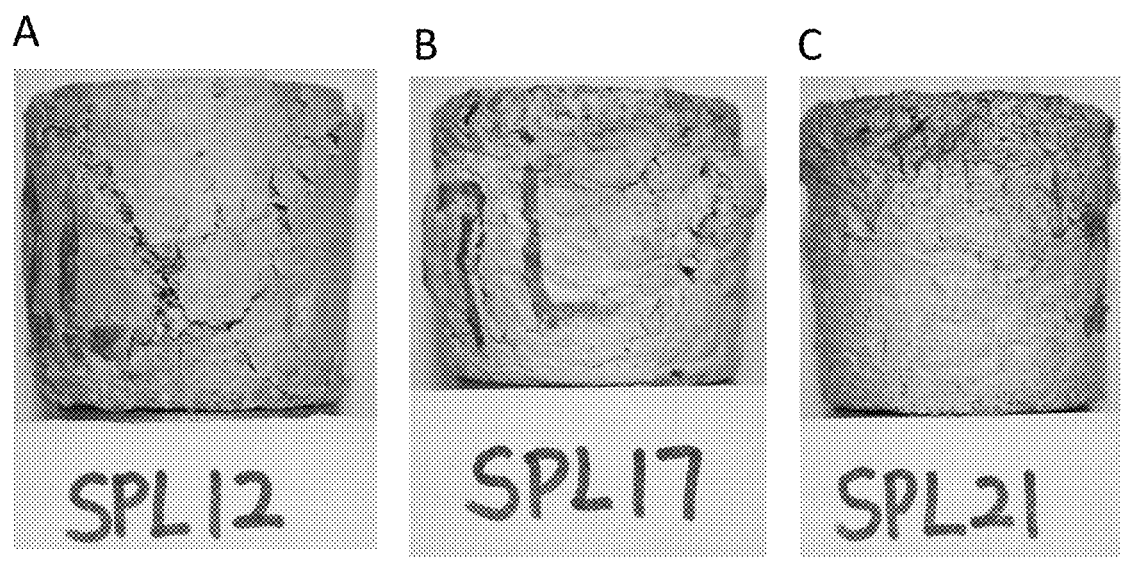
FIG. 8 shows typical failure modes in the white-rot fungal mycelium-based biodegradable insulation material under unconfined compression test: a) Shear failure; and b and c) bulging.

FIGS. 8a, b and c present images of three representative samples (e.g. SPL 12, SPL 17 and SPL 21) after unconfined compression test to show the appearance of the biofoam and illustrate the failure modes of the biofoam under compression. SPL 12 was densely packed without natural fiber, SPL 21 was densely packed with natural fiber visible on the sample, and SPL 17 was loosely packed without natural fiber. One can observe from FIG. 8 that the biodegradable insulation material samples have a chitinous skin formed around all the samples due to the polycarbonate molds which constrained the mycelium growth in the radial direction and stimulated the generation of the outer skin when expanding biomass of mycelium came in contact with molds and formed a fairly strong protection layer on the circumferential surface of the sample. The skin was white when the sample was live and became off-white to beige when the sample was dried in the oven. Such skin did not exist on the top and bottom surfaces of the samples as it was in contact with air during the incubating process. The substrate materials such as sawdust and natural fiber are still visible on the top and bottom of sample surfaces or when the material is cut or cracked.

In general, shear failure was observed for densely packed samples without natural fiber, as shown in FIG. 8a for SPL12, and bulging for loosely packed samples, as evidenced in FIG. 8b for SPL 17. When natural fibers are present, the samples all failed in bulging, regardless of the packing condition, as evidenced in FIG. 8c for SPL 21. One can note that the natural fiber prevented or minimized the surface cracking on the samples during unconfined compressive test. This is important as it would be more difficult for water to seep into the samples under loading. It is also visible from FIG. 8 that loosely packed samples (e.g. SPL 17) experienced substantially more plastic strain than densely packed samples after compression test, as the residual height for SPL 17 was noticeably shorter than the other two samples when their original height was about the same.

ii. Elastic Moduli

Figure 9:
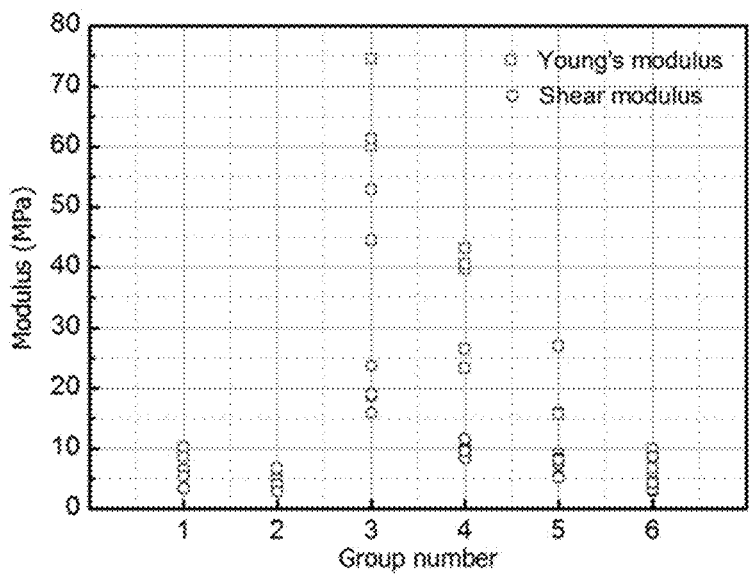
FIG. 9 shows Young's and shear moduli of SP samples in vertical direction
Figure 10:
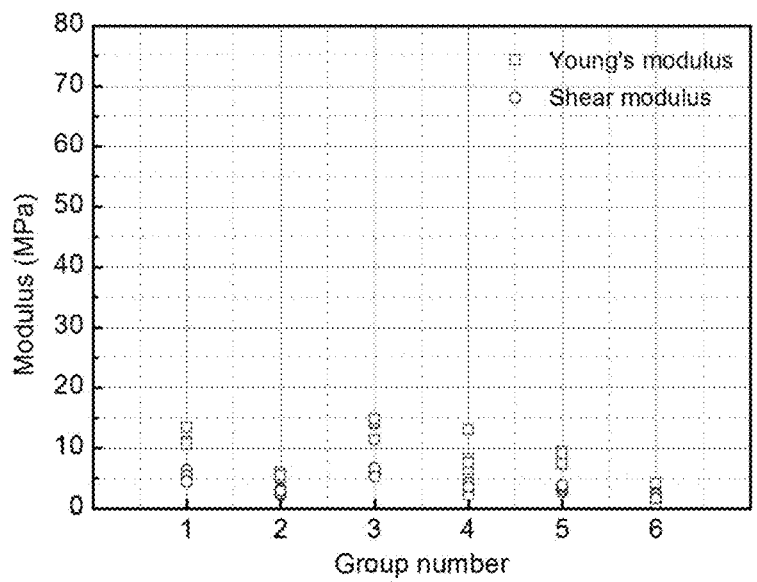
FIG. 10 shows Young's and shear moduli of SL samples in vertical direction.
Figure 11:
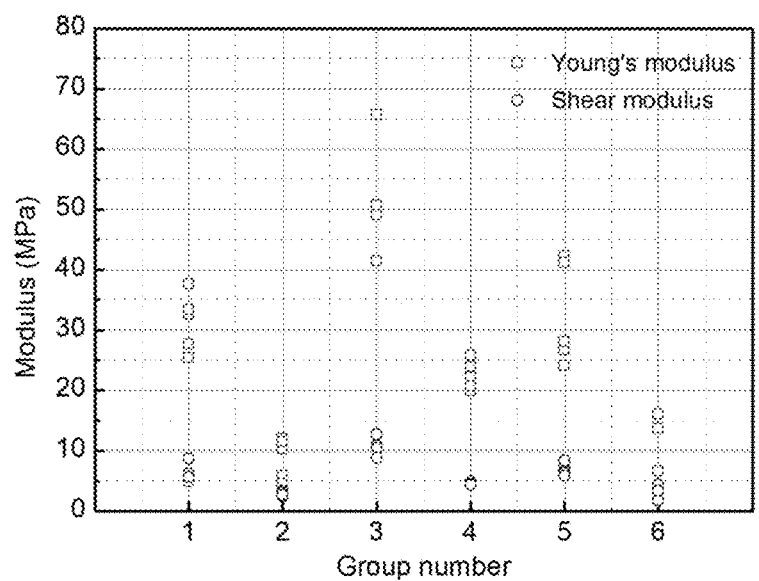
FIG. 11 shows Young's and shear moduli of SPL samples in vertical direction.

The elastic moduli including Young's and shear modulus are basic mechanical properties for evaluating elastic deformation for engineering materials. FIGS. 9, 10 and 11 present Young's and shear moduli in vertical direction for SP, SL and SPL batches of samples. In general Young's modulus for all groups of samples are much higher than shear modulus. The packing condition has obvious impact on the stiffness, with the dense sample exhibiting higher stiffness than loose samples given the same mixing protocol and this impact can also be observed for other physical and mechanical properties presented throughout this study.

One can observe from FIGS. 9-11 that Young's moduli for SP samples are the largest with a peak value of 74 MPa occurring for G3, and those for SL batch samples are the smallest with a peak value of 15 MPa occurring for G3. The largest shear modulus occurs in G3 of SP batch with a peak value of 20 MPa and the smallest shear modulus occurs in SL batch as well. It is easy to observe that shear modulus for G3 samples in SPL batch are substantially smaller than those in SP batch. Comparing FIGS. 9 and 10, one can easily see that the elastic moduli of live samples are substantially smaller than dried samples with the same blend and packing condition. Comparing FIGS. 9 and 11, additional four weeks' incubation time has mixed impact on Young's modulus and mostly negative impact on shear modulus.

iii. Anisotropy of Elastic Moduli

Figure 12:
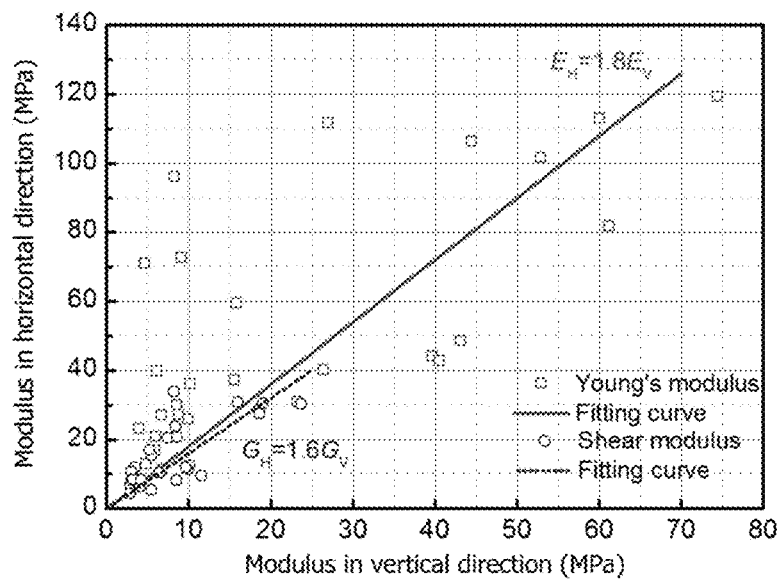
FIG. 12 shows elastic moduli anisotropy of SP samples
Figure 13:
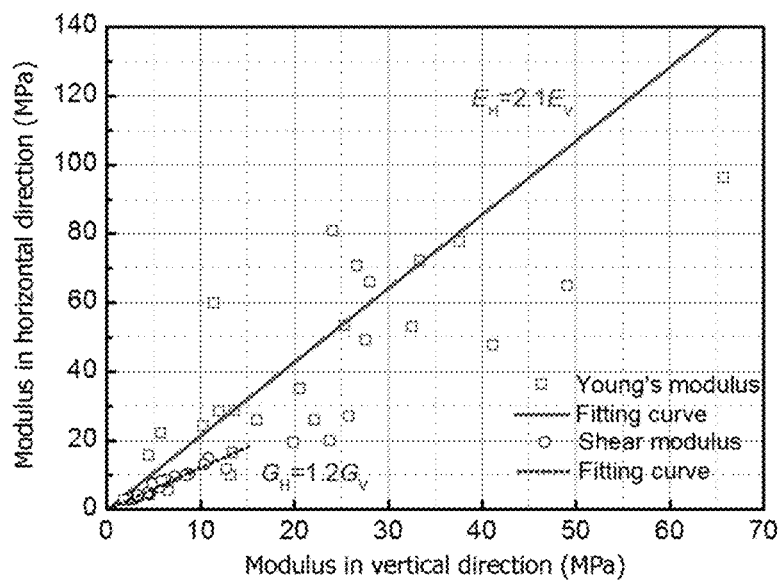
FIG. 13 shows elastic moduli anisotropy of SPL samples.

The elastic moduli was also measured in the horizontal direction with BE and PDE methods. FIGS. 12 and 13 present the elastic moduli in horizontal direction in relation to those in vertical direction for SP and SPL samples, respectively. It is surprising to find that Young's and shear moduli in horizontal direction for all samples in SP and SPL batches is much higher than those in vertical direction. The linear regression equations for SP and SPL samples are presented in FIGS. 12 and 13. Specifically, Young's modulus in horizontal direction EH is about 1.8 to 2.1 times of that in vertical direction, and shear modulus in horizontal direction is about 1.2-1.6 times of that in vertical direction. This strong elastic modulus anisotropy is likely caused by the strong protection skin formed on the circumferential surface of the sample.

iv. Stress-Strain Relationship and Compressive Strength

Figure 14:
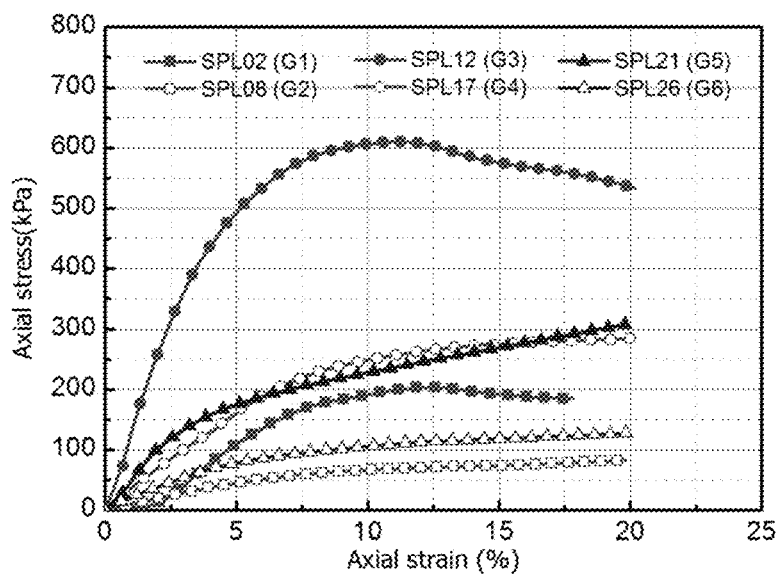
FIG. 14 shows typical stress-strain relationships in unconfined compression test.

Samples in the same groups of SP and SPL batches exhibit similar stress-strain relationships in the unconfined compression test. For example, FIG. 14 shows stress-strain relationships for G1-G6 samples of SPL batch. In general, like for soil materials, the stress-strain curve exhibits strain-softening behavior for densely packed samples such as SPL02 and SPL12, and strain-hardening behavior for loosely packed samples such as SPL08 and SPL17. For the samples with natural fiber included in the substrate such as SPL 21 and SPL26, the stress-strain relationships exhibit strain-hardening behavior regardless of the packing condition, as the natural fiber serve to reinforce the biodegradable insulation material and prevent shear failure from occurring.

Figure 15:
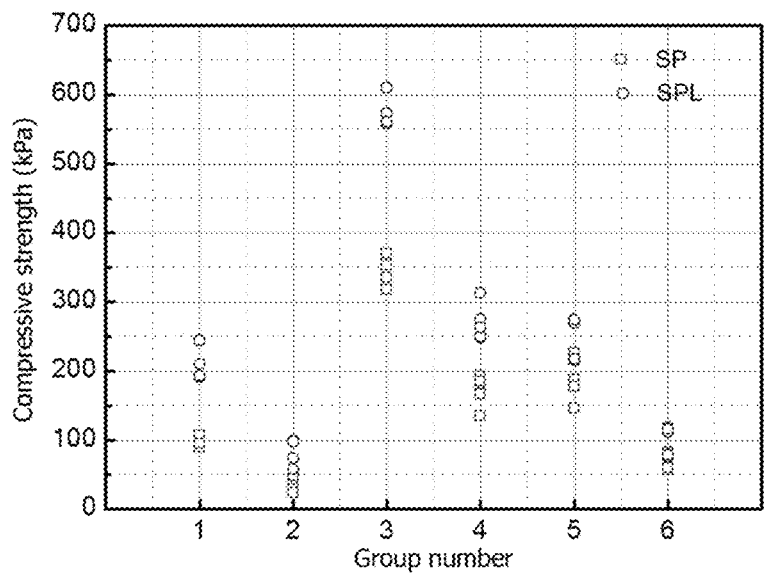
FIG. 15 shows compressive strength of SP and SPL samples.

The compressive strength can be obtained from the stress-strain relationships for each sample. It is defined as the peak stress when a peak occurs in the stress-strain relationship (strain-softening behavior), or the stress at 15% failure strain when no peak occurs in the stress-strain relationship (strain-hardening behavior). FIG. 15 presents the compressive strength of SP and SPL samples. The compressive strengths for G3 samples are substantially larger than other groups in both SP and SPL batches. One can also observe a substantial increase in the compressive strength when the incubation time increases from two weeks to six weeks.

v. Thermal Conductivity

Figure 16:
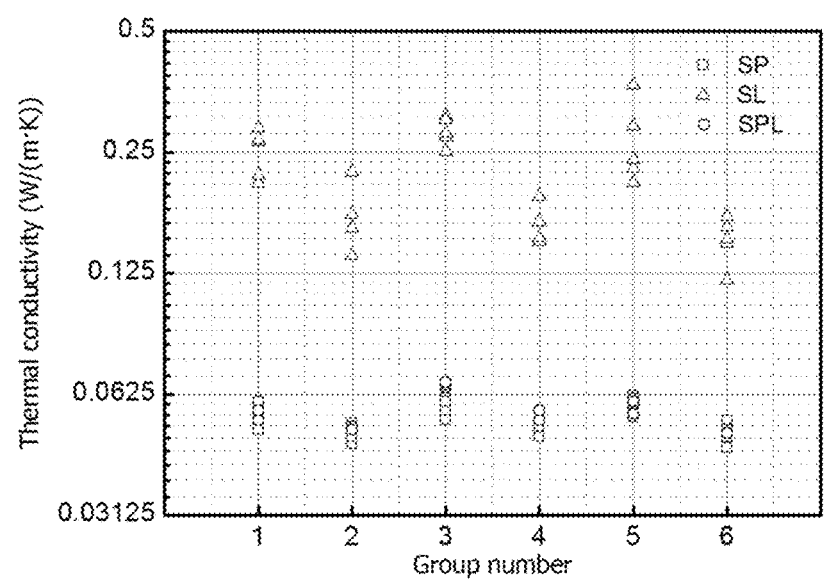
FIG. 16 shows thermal conductivity of SP, SL and SPL samples.

FIG. 16 presents the thermal conductivity of SP, SL and SPL samples. The thermal conductivity values of live samples (SL samples) are in a range of 0.13 to 0.40 W/(m·K), and those of dried samples (SP and SPL samples) fall in a much smaller range, i.e. 0.05 to 0.07 W/(m·K). The large value and variation in thermal conductivity of live samples are due to high moisture content and varying packing condition of the different blends. The variation of thermal conductivity is still visible but much smaller for dried samples. This substantial drop in thermal conductivity for dried samples is expected and is due to the fact that the varying amount of moisture existing in the substrates and mycelium of live samples is replaced with low-thermal-conductivity air during the drying process.

5. Discussion

Figure 17:
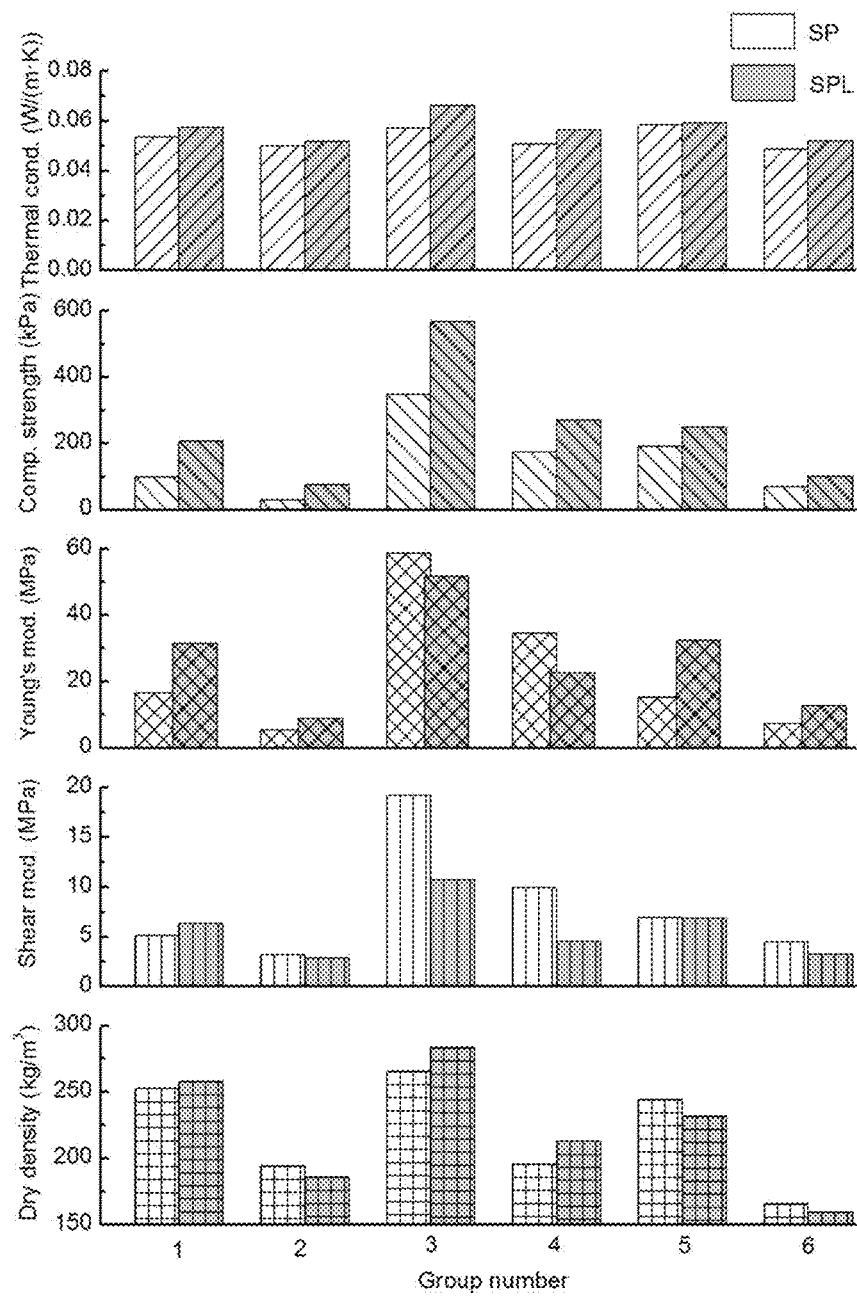
FIG. 17 shows physical, thermal and mechanical properties of mycelium-based biodegradable insulation material.

To allow further examination of the characteristics of different groups of blends, the physical, thermal and mechanical properties such as dry density, shear and Young's moduli, compressive strength, and thermal conductivity of samples in each group were averaged and presented in FIG. 17. Higher values for shear and Young's moduli indicate less elastic deformation and better handling performance during installation, while higher compressive strength suggests less chance of damage when large load is applied. Lower thermal conductivity is desirable for thermal insulation materials. FIG. 17 shows that the average dry density of densely packed samples is in a range of 240~265 kg/m3 for SP samples, and 230~280 kg/m$^3$ for SPL samples. The average dry density of loosely packed samples is in a range of 165~195 kg/m$^3$ for SP samples, and 160~280 kg/m$^3$ for the SPL samples. The dry density of loosely packed samples with natural fiber is considerably lower than those without natural fiber. The impact of additional incubation time on density is mixed with slight increase observed for G1, G3 and G4 samples and slight decrease observed for G2, G5 and G6 samples.

TABLE 2

Physical, thermal and mechanical properties of mycelium-based biofoam

| | SP | | | | |
|---|---|---|---|---|---|
| Group | Density (kg/m$^3$) | Shear modulus (MPa) | Young's modulus (MPa) | Compressive strength (kPa) | Thermal conductivity (W/(m · K)) |
| 1 | 252.71 | 5.10 | 16.55 | 97.20 | 0.054 |
| 2 | 194.13 | 3.20 | 5.39 | 29.50 | 0.050 |
| 3 | 265.63 | 19.20 | 58.63 | 346.70 | 0.057 |
| 4 | 195.72 | 9.93 | 34.62 | 172.10 | 0.051 |
| 5 | 244.43 | 6.93 | 15.15 | 190.80 | 0.059 |
| 6 | 165.69 | 4.50 | 7.25 | 68.70 | 0.049 |

| | SPL | | | | |
|---|---|---|---|---|---|
| Group | Density (kg/m$^3$) | Shear modulus MPa | Young's modulus (MPa) | Compressive strength (kPa) | Thermal conductivity (W/(m · K)) |
| 1 | 257.98 | 6.30 | 31.31 | 206.41 | 0.057 |
| 2 | 185.79 | 2.84 | 8.82 | 75.09 | 0.052 |
| 3 | 283.25 | 10.70 | 51.72 | 567.56 | 0.066 |
| 4 | 213.04 | 4.55 | 22.48 | 269.86 | 0.056 |
| 5 | 231.97 | 6.84 | 32.45 | 249.00 | 0.059 |
| 6 | 159.24 | 3.22 | 12.57 | 100.35 | 0.052 |

One can observe from FIG. 17 that the thermal conductivity of SPL samples is only slightly larger than SP samples, even if the SPL samples were incubated for an additional four weeks. It is quite clear from FIG. 17 that the impact of incubation time on shear modulus is mostly negative except for G1, which sees only slight increase, and mixed on Young's modulus with G3 and G4 samples experiencing decrease and the rest experiencing increase. The shear modulus of G3 samples decreases from 19 MPa to 11 MPa, or 40%. This decrease is very likely due to further fungal digestion of granular substrates such as millet grain and gypsum, which otherwise contributed to the shear stiffness in the earlier stage of mycelium growth. However, the compressive strength for all groups see appreciative gains with increasing incubation time, with the largest absolute value increase occurring for G3 samples, from 350 kPa to 570 kPa, or over 60%. This is very likely due to the growth of mycelium that serves as a random matrix binding together the substrate. In summary, densely packed samples following Mixing Protocol II have the highest dry density, shear and Young's moduli, compressive strength, and comparable thermal conductivity.

As mentioned before, Mixing Protocol III (i.e. samples in G5 and G6) is the same as Mixing Protocol I (i.e. samples in G1 and G2) but with natural fiber added. Comparing the properties of G1 with G5, or G2 with G6 of the same packing condition in either SP or SPL batch, it is interesting to observe that the addition of natural fiber clearly increased the shear modulus and compressive strength, while having mixed impact on the Young's modulus, even when addition of natural fiber decreased the density of samples. The natural fiber plays a positive role in the mycelium-based biodegradable insulation material as it helped increase the shear stiffness, changed the failure mode from potential shear failure to bulging for dense samples, and prevented or reduced occurring of surface cracks.

The properties of these biodegradable insulation materials can be compared to the properties of Insulfoam (ARCAT, Inc., 2012), an expanded polystyrene foam, widely used as insulation material in the building and infrastructure construction industry, particularly in cold regions. The density of Insulfoam is in a range of 16 to 48 kg/m3, its thermal conductivity in a range of 0.03 to 0.04 W/(m·K), and its compressive strength in a range of 69 to 400 kPa. The compressive strength of mycelium-based biodegradable insulation material meets or exceeds that of Insulfoam products and the thermal conductivity is slightly higher. The density is considerably higher than Insulfoam and can be improved by techniques including the scaffold technique for practical applications.

6. Conclusions

This Example shows a fungal mycelium-based biodegradable insulation material, attributes of the same as well as methods of making the same. Three different mixing protocols with various substrate materials including wood pulp, millet grain, wheat bran, natural fiber and calcium sulfate, and two packing conditions were experimented to produce three batches of samples for physical, thermal, and mechanical property characterization. Dry density, thermal conductivity, elastic moduli including shear and Young's moduli, and compressive strength were obtained. Based on the findings from this study the following conclusions can be drawn: 1) The biodegradable insulation materials are relatively light-weight; 2) Results show that densely packed samples following Mixing Protocol II, i.e. G3 samples, have the highest dry density, shear and Young's moduli, and compressive strength; 3) The dried biodegradable insulation materials demonstrate good thermal conductivity, which falls in a range of 0.05 to 0.07 W/(m·K). Live samples possess higher conductivity due to existence of relatively high moisture content; 4) These biodegradable insulation materials exhibit fairly good shear and Young's moduli when it is dried. However, the live sample exhibits much lower elastic moduli; 5) These biodegradable insulation materials exhibit strong elastic anisotropy, with a Young's modulus in horizontal direction 1.8 to 2.1 times that in vertical direction, and a shear modulus in horizontal direction 1.2-1.6 times that in vertical direction. This strong elastic anisotropy can be attributed to a strong protection skin formed on the circumferential surface of samples; 6) These biodegradable insulation materials demonstrates excellent compressive strength with an average value of 350 kPa to 570 kPa for G3 samples; 7) The incubation time has small impact on the dry density and thermal conductivity, mixed impact on Young's modulus, negative impact on the shear modulus, but clear positive impact on the compressive strength; 8) The addition of natural fiber helps improve the shear modulus and compressive strength, and change the failure mode of densely packed samples from shear failure to bulging, and prevent or minimize the occurrence of surface cracks during compression test; and 9) These biodegradable insulation materials have met or exceeded like characteristics of the conventional polymeric thermal foams except dry density.

Those skilled in the art will recognize, or be able to ascertain using no more than routine experimentation, many equivalents to the specific embodiments of the method and compositions described herein. Such equivalents are intended to be encompassed by the following claims.

REFERENCES

Alaska Climate Research Center, U. o. A. F. (2014), Alaska 2014 Statewide Climate Summary, edited, University of Alaska Fairbanks, University of Alaska Fairbanks.

Holt, G. A., G. McIntyre, D. Flagg, E. Bayer, J. D. Wanjura, and M. G. Pelletier (2012), Fungal Mycelium and Cotton Plant Materials in the Manufacture of Biodegradable Molded Packaging Material: Evaluation Study of Select Blends of Cotton Byproducts, Journal of Biobased Materials and Bioenergy, 6(4), 431-439.

Huang Y C, Tsuang W. Health effects associated with faulty application of spray polyurethane foam in residential homes. Environ Res. 2014 October; 134:295-300.

Pan, H., W. Wang, Y. Pan, L. Song, Y. Hu, and K. M. Liew (2015), Formation of self-extinguishing flame retardant biobased coating on cotton fabrics via Layer-by-Layer assembly of chitin derivatives, Carbohydrate polymers, 115, 516-524.

Travaglini, S. N., J. Ross, P. G (2013), Mycology matrix composites, 8th Annual Technical Conference of the American Society for Composites.

Gareis, M. 2006. Diagnostic cell culture assay (MTT-test) for the detection of cytotoxic contaminants and residues (in German). Journal Consumer Protection and Food Safety (J. für Verbraucherschutz and Lebensmittelsicherheit) 1: 354-363.

Johanning, E., M. Gareis, C. S. Yang, E. L. Hintikka, M. Nikulin, B. Jarvis, and R. Dietrich. 1998. Toxicity screening of materials from buildings with fungal indoor air quality problems (*Stachybotrys chartarum*). Mycotoxin Research 14: 60-73.

Hanelt, M., Gareis, M., and Kollarczik, B. (1995) Cytotoxicity evaluation of mycotoxins evaluated by the MTT cell culture assay. Mycopathologia, 128, 167-174.

Zhang H, Kuo Y Y, Gerecke A C, Wang J. Co-release of hexabromocyclododecane (HBCD) and Nano- and microparticles from thermal cutting of polystyrene foams. Environ Sci Technol. 2012 Oct. 16; 46(20):10990-6.

ARCAT, Inc. Insulfoam Specifications, Section 07210, EPS Building Insulation. www.insulfoam.com/specifications. Last accessed Sep. 16, 2015.

G. M. Eben Bayer, Method for producing rapidly renewable chitinous material using fungal fruiting bodies and product made thereby, in The United States Patent and Trademark Office, edited by T. U. S. P. a. T. Office, US, 2011.

A. Bandyopadhyay, G. C. Basak, Studies on photocatalytic degradation of polystyrene, Materials Science and Technology, 23(3) (2007) 307-314.

T. Hofer, Marine pollution: new research, in Marine pollution: new research, edited, p. 59, Nova Science Publishers, New York, 2008.

S. Travaglini, J. Noble, P. G. Ross, C. K. H. Dharan, Mycology matrix composites. Proc. 28th Annual Technical Conference of the American Society for Composites. 1 (2013) 517-535.

Y. H. Arifin, Y. Yusuf, "Mycelium fibers as new resource for environmental sustainability." procedia engineering: Malaysian Technical Universities Conference on Engineering & Technology. 53 (2013) 504-508.

G. A. Holt, G. McIntyre, D. Glagg, J. D. Wanjura, M. G. Pelletier, fungal mycelium and cotton plant materials in the manufacture of biodegradable molded packaging material: evaluation study of select blends of cotton byproducts, Journal of Biobased Materials and Bioenergy, 6 (2012) 431-439.

M. G. Pelletier, G. A. Hol, J. D. Wanjura, E. Bayer, G. McIntyre, "An evaluation study of mycelium based acoustic absorbers grown on agricultural by-product substrates." Industrial Crops and Products, 51 (2013) 480-485.

S. Travaglini, C. Dharan, P. G. Ross, Mycology matrix composites. Proc. 29th Technical Conference of the American Society for Composites, 2014.

Decagon Devices, Inc., Operator's Manual for KD2 Pro Thermal Properties Analyzer, Pullman Wash., 2015.

ASTM D5334-14, Standard Test Method for Determination of Thermal Conductivity of Soil and Soft Rock by Thermal Needle Probe Procedure, ASTM International, West Conshohocken, Pa., www.astm.org, 2014.

ASTM D2166-13, Standard Test Method for Unconfined Compressive Strength of Cohesive Soil, ASTM International, West Conshohocken, Pa. www.astm.org, 2013.

D. J. Shirley, A. L. Anderson, Acoustic and engineering properties of sediments. Report ARL-TR-75-58. Applied Research Laboratory, University of Texas, Austin, 1975.

P. De Alba, K. Baldwin, V. Janoo, G. Roe, B. Celikkol, Elastic-Wave Velocities and Liquefaction Potential. Geotechnical Testing Journal, ASTM, 7(2) (1984) 77-88.

R. Dyvik, C. Madshus, Lab measurements of $G_{max}$ using bender element, Proc., ASCE Convention on Advances in the Art of Testing Soils under Cyclic Conditions, (1985) 186-196.

J. S. Lee, J. Carlos Santamarina, Bender elements: performance and signal interpretation, Journal of Geotechnical and Geoenvironmental Engineering, 131 (9) (2005) 1063-1070.

E. C. Leong, S. H. Yeo, H. Rahardjo, Measuring shear wave velocity using bender elements. Geotechnical Testing Journal, 28(5) (2005) 1-11.

E. Eseller-Bayat, S. Gokyer, M. K. Yegian, R. O. Deniz, A. Alshawabkeh, Bender elements and bending disks for measurement of shear and compression wave velocities in large fully and partially saturated sand specimens. Geotechnical Testing Journal, 36(2) (2013) 1-8.

Veronica M. Padula, Sydney Stewart, and Douglas Causey. The impacts of plastic on western Aleutian Islands seabirds: detection of phthalates in muscle and embryonic tissues. Proceedings of the 16th Alaska Bird Conference, Juneau, Ak., USA; 2014.

K. V. Harish Prashanth and R. N. Tharanathan. Chitin/chitosan: modifications and their unlimited application potential—an overview. Trends in Food Science & Technology. 18 (2007) 117-131.

Shirley and Anderson 1975; De Alba et al. 1984; Dyvik and Madshus 1985; Lee and Santamarina 2005; Leong et al. 2005; Eseller-Bayat et al. 2013

We claim:

1. A biodegradable insulation material comprising
   a. a structural scaffold comprising a three-dimensional structure and a mycelium from a first temperature resilient fungus, wherein the mycelium from the first temperature resilient fungus has colonized the three-dimensional structure, wherein the structural scaffold has a chitinous hydrophobic outer skin; and b. a substrate comprising nutritive media and a mycelium from a second temperature resilient fungus, wherein the mycelium from the second temperature resilient fungus has colonized the substrate;

wherein the biodegradable insulation material is the result of the structural scaffold and substrate fusing together, wherein the first temperature resilient fungus and second temperature resilient fungus are different.

2. The biodegradable insulation material of claim 1, wherein the substrate comprises a biomass feedstock.

3. The biodegradable insulation material of claim 1, wherein the structural scaffold comprises a structural reinforcement.

4. The biodegradable insulation material of claim 1, wherein the biodegradable insulation material comprises the net shape of an object to be insulated.

5. The biodegradable insulation material of claim 4, wherein the biodegradable insulation material comprises the net shape of a cylinder, tube, circle, oval, rectangle, or square.

6. The biodegradable insulation material of claim 1, wherein the structural scaffold comprises the net shape of an object to be insulated.

7. The biodegradable insulation material of claim 1, wherein the structural scaffold comprises a biopolymer or synthetic polymer that is non-toxic to the fungus and withstands moisture and humidity.

8. The biodegradable insulation material of claim 7, wherein the biopolymer is a cellulose-based biopolymer filament.

9. The biodegradable insulation material of claim 1, further comprising mycelium from a second temperature resilient fungus.

10. The biodegradable insulation material of claim 1, wherein the at least one of the first and second temperature resilient fungi is a fungus that remains biologically viable within a temperature range of +30° to −50° C.

11. The biodegradable insulation material of claim 1, wherein at least one of the first or second temperature resilient fungus is a saprotrophic Basidiomycete.

12. The biodegradable insulation material of claim 11, wherein the saprotrophic Basidiomycete is a polypore.

13. The biodegradable insulation material of claim 12, wherein the polypore is *Irpex lacteus*.

14. A method of insulating an infrastructure comprising introducing the biodegradable insulation material of claim 1 to an infrastructure.

15. A biodegradable insulation material comprising
a. a structural scaffold comprising a sterilized biodegradable three-dimensional mesh that is non-toxic to the fungus and a mycelium from a first temperature resilient fungus, wherein the mycelium from the first temperature resilient fungus has colonized the three-dimensional mesh, wherein the structural scaffold has a chitinous hydrophobic outer skin; and
b. a substrate comprising nutritive media and a second temperature resilient fungus, wherein the mycelium from a second temperature resilient fungus has colonized the substrate;

wherein the biodegradable insulation material is the result of the structural scaffold and substrate fusing together, wherein the first temperature resilient fungus and second temperature resilient fungus are from different temperature resilient fungi.

* * * * *